(12) United States Patent
Eckert et al.

(10) Patent No.: US 8,303,962 B2
(45) Date of Patent: Nov. 6, 2012

(54) ANTIBACTERIAL AND ANTIFUNGAL PEPTIDES

(75) Inventors: Randal H. Eckert, Redondo Beach, CA (US); Chris Kaplan, Los Angeles, CA (US); Jian He, Los Angeles, CA (US); Daniel K. Yarbrough, Los Angeles, CA (US); Maxwell Anderson, Sequim, WA (US); Jee-Hyun Sim, Garden Grove, CA (US)

(73) Assignee: C3 Jian, Inc., Inglewood, CA (US)

( * ) Notice: Subject to any disclaimer, the term of this patent is extended or adjusted under 35 U.S.C. 154(b) by 0 days.

(21) Appl. No.: 12/683,188

(22) Filed: Jan. 6, 2010

(65) Prior Publication Data

US 2010/0184681 A1    Jul. 22, 2010

Related U.S. Application Data

(60) Provisional application No. 61/142,830, filed on Jan. 6, 2009, provisional application No. 61/151,445, filed on Feb. 10, 2009, provisional application No. 61/243,905, filed on Sep. 18, 2009, provisional application No. 61/243,930, filed on Sep. 18, 2009.

(51) Int. Cl.
| | |
|---|---|
| A61K 38/00 | (2006.01) |
| A61K 38/04 | (2006.01) |
| A61K 39/00 | (2006.01) |
| A61K 39/02 | (2006.01) |
| A61K 39/09 | (2006.01) |
| A61K 39/38 | (2006.01) |
| C07K 4/00 | (2006.01) |
| C07K 5/00 | (2006.01) |
| C07K 7/00 | (2006.01) |

(52) U.S. Cl. ............... 424/244.1; 424/184.1; 424/185.1; 424/190.1; 424/234.1; 424/237.1; 424/282.1; 530/300; 530/326; 930/10; 930/20; 930/21; 930/200

(58) Field of Classification Search ....................... None
See application file for complete search history.

(56) References Cited

U.S. PATENT DOCUMENTS

| | | |
|---|---|---|
| 2002/0082195 A1 | 6/2002 | Lehrer et al. |
| 2002/0156017 A1 | 10/2002 | Hancock et al. |
| 2002/0166141 A1 | 11/2002 | Simmons et al. |
| 2003/0105281 A1 | 6/2003 | Noga et al. |
| 2003/0144184 A1 | 7/2003 | Lehrer et al. |
| 2003/0148397 A1 | 8/2003 | Leite et al. |
| 2003/0195150 A1 | 10/2003 | Reynolds et al. |
| 2004/0033955 A1 | 2/2004 | Catania et al. |

(Continued)

FOREIGN PATENT DOCUMENTS

WO    WO2010/080819    7/2010

(Continued)

OTHER PUBLICATIONS

PCT International Search Report and Written Opinion dated Mar. 30, 2010 issued in WO2010/080819 [PCT/US2010/020242].

(Continued)

Primary Examiner — Ja'Na Hines
(74) Attorney, Agent, or Firm — Tom Hunter; Weaver Austin Villeneuve & Sampson LLP

(57) ABSTRACT

This invention provides novel antimicrobial peptides and formulations thereof. The peptides and/or formulations are effective to kill or to inhibit the growth and/or proliferation of various bacteria, yeast, and fungi.

9 Claims, 1 Drawing Sheet

U.S. PATENT DOCUMENTS

| | | |
|---|---|---|
| 2004/0048792 A1 | 3/2004 | Pereira et al. |
| 2004/0052814 A1 | 3/2004 | Shi et al. |
| 2004/0072777 A1 | 4/2004 | Froelich et al. |
| 2004/0072990 A1 | 4/2004 | Tzeng et al. |
| 2004/0087771 A1 | 5/2004 | Lamberty et al. |
| 2004/0235745 A1 | 11/2004 | Deber et al. |
| 2005/0020813 A1* | 1/2005 | Masignani et al. ............ 530/350 |
| 2005/0065072 A1 | 3/2005 | Keeler et al. |
| 2005/0187151 A1 | 8/2005 | Strom et al. |
| 2005/0272645 A1 | 12/2005 | Lehrer et al. |
| 2006/0089488 A1 | 4/2006 | Yoshida et al. |
| 2006/0122122 A1 | 6/2006 | Kobayashi et al. |
| 2006/0128614 A1 | 6/2006 | Cheng et al. |
| 2006/0166883 A1 | 7/2006 | Hu et al. |
| 2006/0287232 A1 | 12/2006 | Clayberger et al. |
| 2007/0032431 A1 | 2/2007 | Yoshida et al. |
| 2007/0178116 A1* | 8/2007 | Adderson et al. ........... 424/190.1 |
| 2007/0231833 A1 | 10/2007 | Arcidiacono et al. |
| 2007/0244044 A1 | 10/2007 | O'Neil et al. |
| 2007/0259087 A1 | 11/2007 | Segura et al. |
| 2008/0069849 A1 | 3/2008 | Schmidtchen et al. |
| 2008/0125359 A1 | 5/2008 | Wang et al. |
| 2008/0170991 A1 | 7/2008 | Shi et al. |
| 2008/0207522 A1 | 8/2008 | Hancock et al. |
| 2008/0213430 A1 | 9/2008 | Segura et al. |
| 2008/0234188 A1 | 9/2008 | Deber et al. |
| 2008/0249022 A1 | 10/2008 | Grote et al. |
| 2008/0286210 A1 | 11/2008 | He et al. |
| 2009/0005300 A1 | 1/2009 | Hodges et al. |
| 2009/0023641 A1 | 1/2009 | O'Neil et al. |
| 2009/0048167 A1 | 2/2009 | Hillman et al. |
| 2009/0074864 A1 | 3/2009 | Schmidtchen et al. |
| 2009/0099533 A1 | 4/2009 | Montelaro et al. |
| 2009/0143299 A1 | 6/2009 | Schmidtchen et al. |
| 2009/0156499 A1 | 6/2009 | Wang et al. |
| 2009/0214498 A1 | 8/2009 | Ross et al. |
| 2009/0233870 A1 | 9/2009 | Blondelle et al. |
| 2009/0258045 A1 | 10/2009 | Chuang et al. |
| 2009/0264344 A1 | 10/2009 | Lehrer et al. |
| 2009/0312265 A1 | 12/2009 | Schmidtchen et al. |
| 2010/0184683 A1 | 7/2010 | Eckert et al. |
| 2010/0184684 A1 | 7/2010 | Eckert et al. |
| 2011/0039761 A1 | 2/2011 | Eckert et al. |
| 2011/0039762 A1 | 2/2011 | Eckert et al. |
| 2011/0039763 A1 | 2/2011 | Eckert et al. |

FOREIGN PATENT DOCUMENTS

| | | |
|---|---|---|
| WO | WO2010/080836 | 7/2010 |

OTHER PUBLICATIONS

PCT International Preliminary Report on Patentability dated Jul. 12, 2011 issued in WO2010/080819 [PCT/US2010/020242].

Eckert et al. (2006) "Adding Selectivity to Antimicrobial Peptides: Rational Design of a Multidomain Peptide against *Pseudomonas* spp." *Antimicrobial Agents and Chemotherapy*, 50(4): 1480-1488.

Eckert et al. (2006) "Enhancement of Antimicrobial Activity against *Pseudomonas aeruginosa* by Coadministration of G10KHc and Tobramycin" *Antimicrobial Agents and Chemotherapy*, 50(11): 3833-3838.

Eckert et al. (2006) "Targeted Killing of *Streptococcus* mutans by a Pheromone-Guided "Smart" Antimicrobial Peptide" *Antimicrobial Agents and Chemotherapy*, 50(11): 3651-3657.

Eckert et al. (2007) "Stability and Activity in Sputum of G10KHc, a Potent Anti-Pseudomonas Antimicrobial Peptide" *Chem Biol Drug Des*, 70: 456-460.

Franzman (2007) "Targeted antimicrobial activity of SMAP28 conjugated to IgG antibody." Master's thesis, University of Iowa, 1-96 http://ir.uiowa.edu/etd/140.

He et al. (2009) "Design and activity of a 'dual-targeted' antimicrobial peptide" *Int. J. Antimicrobial Agents*, 33(6): 532-537.

He et al. (2010) "Systematic Approach to Optimizing Specifically Targeted Antimicrobial Peptides against *Streptococcus* mutans" *Antimicrobial Agents and Chemotherapy*, 54(4): 2143-2151.

Kaplan et al. (2011) "Selective Membrane Disruption: Mode of Action of C16G2, a Specifically Targeted Antimicrobial Peptide" *Antimicrobial Agents and Chemotherapy*, 55(7):3446-3452.

Li et al. (2010) "Targeted Antimicrobial Therapy Against *Streptococcus* mutans Establishes Protective Non-cariogenic Oral Biofilms and Reduces Subsequent Infection" *Int J Oral Sci*, 2(2): 66-73.

\* cited by examiner

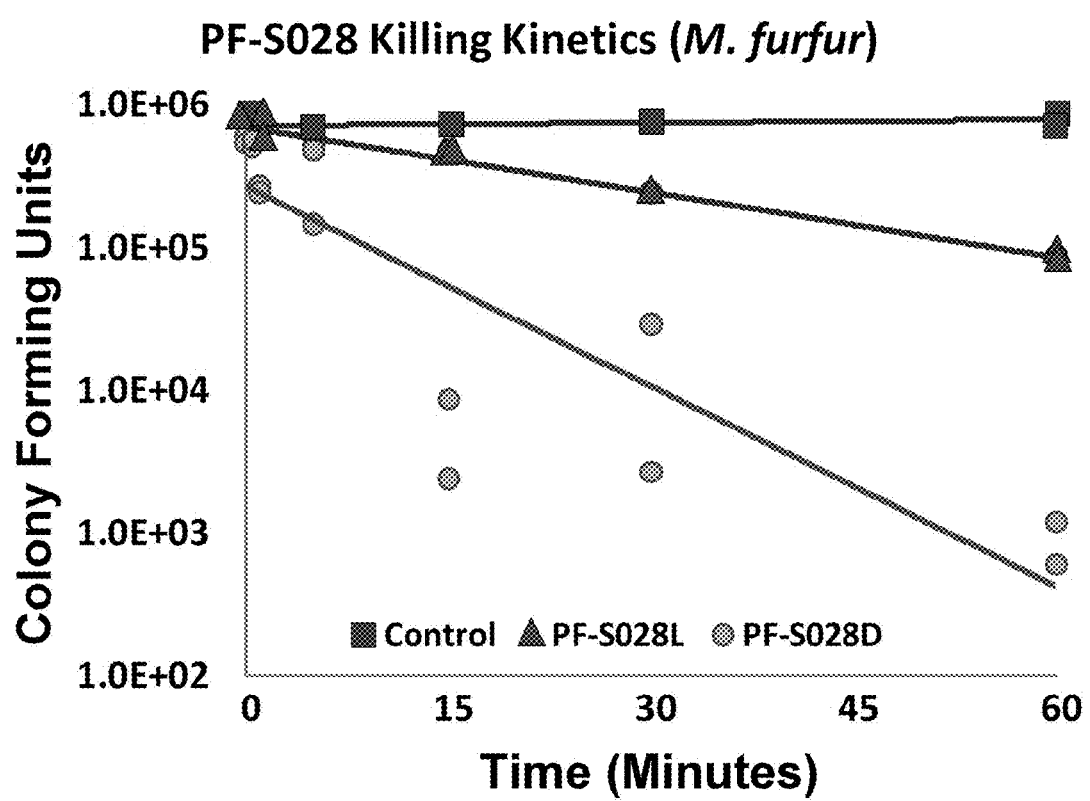

US 8,303,962 B2

SEQUENCE LISTING

```
<160> NUMBER OF SEQ ID NOS: 105

<210> SEQ ID NO 1
<211> LENGTH: 32
<212> TYPE: PRT
<213> ORGANISM: Artificial
<220> FEATURE:
<223> OTHER INFORMATION: Antimicrobial peptide and/or targeting peptide

<400> SEQUENCE: 1

Gly Ser Val Ile Lys Lys Arg Arg Lys Arg Met Ser Lys Lys Lys His
1               5                   10                  15

Arg Lys Met Leu Arg Arg Thr Arg Val Gln Arg Arg Lys Leu Gly Lys
            20                  25                  30

<210> SEQ ID NO 2
```

```
<211> LENGTH: 20
<212> TYPE: PRT
<213> ORGANISM: Artificial
<220> FEATURE:
<223> OTHER INFORMATION: Antimicrobial peptide and/or targeting peptide

<400> SEQUENCE: 2

Asn Tyr Arg Leu Val Asn Ala Ile Phe Ser Lys Ile Phe Lys Lys
1               5                   10                  15

Phe Ile Lys Phe
            20

<210> SEQ ID NO 3
<211> LENGTH: 21
<212> TYPE: PRT
<213> ORGANISM: Artificial
<220> FEATURE:
<223> OTHER INFORMATION: Antimicrobial peptide and/or targeting peptide

<400> SEQUENCE: 3

Tyr Ile Gln Phe His Leu Asn Gln Gln Pro Arg Pro Lys Val Lys Lys
1               5                   10                  15

Ile Lys Ile Phe Leu
            20

<210> SEQ ID NO 4
<211> LENGTH: 32
<212> TYPE: PRT
<213> ORGANISM: Artificial
<220> FEATURE:
<223> OTHER INFORMATION: Antimicrobial peptide and/or targeting peptide

<400> SEQUENCE: 4

Gly Ser Val Ile Lys Lys Arg Arg Lys Arg Met Ala Lys Lys Lys His
1               5                   10                  15

Arg Lys Leu Leu Lys Lys Thr Arg Ile Gln Arg Arg Arg Ala Gly Lys
            20                  25                  30

<210> SEQ ID NO 5
<211> LENGTH: 30
<212> TYPE: PRT
<213> ORGANISM: Artificial
<220> FEATURE:
<223> OTHER INFORMATION: Antimicrobial peptide and/or targeting peptide

<400> SEQUENCE: 5

Met Arg Phe Gly Ser Leu Ala Leu Val Ala Tyr Asp Ser Ala Ile Lys
1               5                   10                  15

His Ser Trp Pro Arg Pro Ser Ser Val Arg Arg Leu Arg Met
            20                  25                  30

<210> SEQ ID NO 6
<211> LENGTH: 39
<212> TYPE: PRT
<213> ORGANISM: Artificial
<220> FEATURE:
<223> OTHER INFORMATION: Antimicrobial peptide and/or targeting peptide

<400> SEQUENCE: 6

Phe Glu Ser Lys Ile Leu Asn Ala Ser Lys Glu Leu Asp Lys Glu Lys
1               5                   10                  15

Lys Val Asn Thr Ala Leu Ser Phe Asn Ser His Gln Asp Phe Ala Lys
            20                  25                  30

Ala Tyr Gln Asn Gly Lys Ile
            35
```

<210> SEQ ID NO 7
<211> LENGTH: 20
<212> TYPE: PRT
<213> ORGANISM: Artificial
<220> FEATURE:
<223> OTHER INFORMATION: Antimicrobial peptide and/or targeting peptide

<400> SEQUENCE: 7

Lys Gly Lys Ser Leu Met Pro Leu Leu Lys Gln Ile Asn Gln Trp Gly
1               5                   10                  15

Lys Leu Tyr Leu
            20

<210> SEQ ID NO 8
<211> LENGTH: 18
<212> TYPE: PRT
<213> ORGANISM: Artificial
<220> FEATURE:
<223> OTHER INFORMATION: Antimicrobial peptide and/or targeting peptide

<400> SEQUENCE: 8

Trp Ser Arg Val Pro Gly His Ser Asp Thr Gly Trp Lys Val Trp His
1               5                   10                  15

Arg Trp

<210> SEQ ID NO 9
<211> LENGTH: 21
<212> TYPE: PRT
<213> ORGANISM: Artificial
<220> FEATURE:
<223> OTHER INFORMATION: Antimicrobial peptide and/or targeting peptide

<400> SEQUENCE: 9

Met Gly Ile Ile Ala Gly Ile Ile Lys Phe Ile Lys Gly Leu Ile Glu
1               5                   10                  15

Lys Phe Thr Gly Lys
            20

<210> SEQ ID NO 10
<211> LENGTH: 29
<212> TYPE: PRT
<213> ORGANISM: Artificial
<220> FEATURE:
<223> OTHER INFORMATION: Antimicrobial peptide and/or targeting peptide

<400> SEQUENCE: 10

Ile Leu Asn Lys Lys Pro Lys Leu Pro Leu Trp Lys Leu Gly Lys Asn
1               5                   10                  15

Tyr Phe Arg Arg Phe Tyr Val Leu Pro Thr Phe Leu Ala
            20                  25

<210> SEQ ID NO 11
<211> LENGTH: 16
<212> TYPE: PRT
<213> ORGANISM: Artificial
<220> FEATURE:
<223> OTHER INFORMATION: Antimicrobial peptide and/or targeting peptide

<400> SEQUENCE: 11

Arg Glu Ser Lys Leu Ile Ala Met Ala Asp Met Ile Arg Arg Arg Ile
1               5                   10                  15

<210> SEQ ID NO 12
<211> LENGTH: 37

```
<212> TYPE: PRT
<213> ORGANISM: Artificial
<220> FEATURE:
<223> OTHER INFORMATION: Antimicrobial peptide and/or targeting peptide

<400> SEQUENCE: 12

Leu Asp Pro Leu Glu Pro Arg Ile Ala Pro Pro Gly Asp Arg Ser His
1               5                   10                  15

Gln Gly Ala Pro Ala Cys His Arg Asp Pro Leu Arg Gly Arg Ser Ala
            20                  25                  30

Arg Asp Ala Glu Arg
        35

<210> SEQ ID NO 13
<211> LENGTH: 51
<212> TYPE: PRT
<213> ORGANISM: Artificial
<220> FEATURE:
<223> OTHER INFORMATION: Antimicrobial peptide and/or targeting peptide

<400> SEQUENCE: 13

Met Pro Val Ser Lys Lys Arg Tyr Met Leu Ser Ser Ala Tyr Ala Thr
1               5                   10                  15

Ala Leu Gly Ile Cys Tyr Gly Gln Val Ala Thr Asp Glu Lys Glu Ser
            20                  25                  30

Glu Ile Thr Ala Ile Pro Asp Leu Leu Asp Tyr Leu Ser Val Glu Glu
        35                  40                  45

Tyr Leu Leu
    50

<210> SEQ ID NO 14
<211> LENGTH: 24
<212> TYPE: PRT
<213> ORGANISM: Artificial
<220> FEATURE:
<223> OTHER INFORMATION: Antimicrobial peptide and/or targeting peptide

<400> SEQUENCE: 14

Leu Ser Leu Ala Thr Phe Ala Lys Ile Phe Met Thr Arg Ser Asn Trp
1               5                   10                  15

Ser Leu Lys Arg Phe Asn Arg Leu
            20

<210> SEQ ID NO 15
<211> LENGTH: 30
<212> TYPE: PRT
<213> ORGANISM: Artificial
<220> FEATURE:
<223> OTHER INFORMATION: Antimicrobial peptide and/or targeting peptide

<400> SEQUENCE: 15

Met Ile Arg Ile Arg Ser Pro Thr Lys Lys Lys Leu Asn Arg Asn Ser
1               5                   10                  15

Ile Ser Asp Trp Lys Ser Asn Thr Ser Gly Arg Phe Phe Tyr
            20                  25                  30

<210> SEQ ID NO 16
<211> LENGTH: 37
<212> TYPE: PRT
<213> ORGANISM: Artificial
<220> FEATURE:
<223> OTHER INFORMATION: Antimicrobial peptide and/or targeting peptide

<400> SEQUENCE: 16
```

```
Met Lys Arg Arg Arg Cys Asn Trp Cys Gly Lys Leu Phe Tyr Leu Glu
1               5                   10                  15

Glu Lys Ser Lys Glu Ala Tyr Cys Cys Lys Glu Cys Arg Lys Lys Ala
            20                  25                  30

Lys Lys Val Lys Lys
        35

<210> SEQ ID NO 17
<211> LENGTH: 28
<212> TYPE: PRT
<213> ORGANISM: Artificial
<220> FEATURE:
<223> OTHER INFORMATION: Antimicrobial peptide and/or targeting peptide

<400> SEQUENCE: 17

Val Leu Pro Phe Pro Ala Ile Pro Leu Ser Arg Arg Arg Ala Cys Val
1               5                   10                  15

Ala Ala Pro Arg Pro Arg Ser Arg Gln Arg Ala Ser
            20                  25

<210> SEQ ID NO 18
<211> LENGTH: 30
<212> TYPE: PRT
<213> ORGANISM: Artificial
<220> FEATURE:
<223> OTHER INFORMATION: Antimicrobial peptide and/or targeting peptide

<400> SEQUENCE: 18

Lys Asn Lys Lys Gln Thr Asp Ile Leu Glu Lys Val Lys Glu Ile Leu
1               5                   10                  15

Asp Lys Lys Lys Thr Lys Ser Val Gly Gln Lys Leu Tyr
            20                  25                  30

<210> SEQ ID NO 19
<211> LENGTH: 15
<212> TYPE: PRT
<213> ORGANISM: Artificial
<220> FEATURE:
<223> OTHER INFORMATION: Antimicrobial peptide and/or targeting peptide

<400> SEQUENCE: 19

Ser Leu Gln Ser Gln Leu Gly Pro Cys Leu His Asp Gln Arg His
1               5                   10                  15

<210> SEQ ID NO 20
<211> LENGTH: 30
<212> TYPE: PRT
<213> ORGANISM: Artificial
<220> FEATURE:
<223> OTHER INFORMATION: Antimicrobial peptide and/or targeting peptide

<400> SEQUENCE: 20

Trp Lys Arg Leu Trp Pro Ala Arg Ile Leu Ala Gly His Ser Arg Arg
1               5                   10                  15

Arg Met Arg Trp Met Val Val Trp Arg Tyr Phe Ala Ala Thr
            20                  25                  30

<210> SEQ ID NO 21
<211> LENGTH: 28
<212> TYPE: PRT
<213> ORGANISM: Artificial
<220> FEATURE:
<223> OTHER INFORMATION: Antimicrobial peptide and/or targeting peptide

<400> SEQUENCE: 21
```

```
Lys Phe Gln Gly Glu Phe Thr Asn Ile Gly Gln Ser Tyr Ile Val Ser
1               5                   10                  15

Ala Ser His Met Ser Thr Ser Leu Asn Thr Gly Lys
            20                  25

<210> SEQ ID NO 22
<211> LENGTH: 41
<212> TYPE: PRT
<213> ORGANISM: Artificial
<220> FEATURE:
<223> OTHER INFORMATION: Antimicrobial peptide and/or targeting peptide

<400> SEQUENCE: 22

Thr Lys Lys Ile Glu Leu Lys Arg Phe Val Asp Ala Phe Val Lys Lys
1               5                   10                  15

Ser Tyr Glu Asn Tyr Ile Leu Glu Arg Glu Leu Lys Lys Leu Ile Lys
            20                  25                  30

Ala Ile Asn Glu Glu Leu Pro Thr Lys
        35                  40

<210> SEQ ID NO 23
<211> LENGTH: 20
<212> TYPE: PRT
<213> ORGANISM: Artificial
<220> FEATURE:
<223> OTHER INFORMATION: Antimicrobial peptide and/or targeting peptide

<400> SEQUENCE: 23

Lys Phe Ser Asp Gln Ile Asp Lys Gly Gln Asp Ala Leu Lys Asp Lys
1               5                   10                  15

Leu Gly Asp Leu
            20

<210> SEQ ID NO 24
<211> LENGTH: 13
<212> TYPE: PRT
<213> ORGANISM: Artificial
<220> FEATURE:
<223> OTHER INFORMATION: Antimicrobial peptide and/or targeting peptide

<400> SEQUENCE: 24

Leu Ser Glu Met Glu Arg Arg Arg Leu Arg Lys Arg Ala
1               5                   10

<210> SEQ ID NO 25
<211> LENGTH: 25
<212> TYPE: PRT
<213> ORGANISM: Artificial
<220> FEATURE:
<223> OTHER INFORMATION: Antimicrobial peptide and/or targeting peptide

<400> SEQUENCE: 25

Arg Arg Gly Cys Thr Glu Arg Leu Arg Arg Met Ala Arg Arg Asn Ala
1               5                   10                  15

Trp Asp Leu Tyr Ala Glu His Phe Tyr
            20                  25

<210> SEQ ID NO 26
<211> LENGTH: 26
<212> TYPE: PRT
<213> ORGANISM: Artificial
<220> FEATURE:
<223> OTHER INFORMATION: Antimicrobial peptide and/or targeting peptide

<400> SEQUENCE: 26
```

```
Ser Lys Phe Lys Val Leu Arg Lys Ile Ile Lys Glu Tyr Lys Gly
1               5                   10                  15

Glu Leu Met Leu Ser Ile Gln Lys Gln Arg
            20                  25
```

<210> SEQ ID NO 27
<211> LENGTH: 20
<212> TYPE: PRT
<213> ORGANISM: Artificial
<220> FEATURE:
<223> OTHER INFORMATION: Antimicrobial peptide and/or targeting peptide

<400> SEQUENCE: 27

```
Phe Glu Leu Val Asp Trp Leu Glu Thr Asn Leu Gly Lys Ile Leu Lys
1               5                   10                  15

Ser Lys Ser Ala
            20
```

<210> SEQ ID NO 28
<211> LENGTH: 22
<212> TYPE: PRT
<213> ORGANISM: Artificial
<220> FEATURE:
<223> OTHER INFORMATION: Antimicrobial peptide and/or targeting peptide

<400> SEQUENCE: 28

```
Leu Val Leu Arg Ile Cys Thr Asp Leu Phe Thr Phe Ile Lys Trp Thr
1               5                   10                  15

Ile Lys Gln Arg Lys Ser
            20
```

<210> SEQ ID NO 29
<211> LENGTH: 24
<212> TYPE: PRT
<213> ORGANISM: Artificial
<220> FEATURE:
<223> OTHER INFORMATION: Antimicrobial peptide and/or targeting peptide

<400> SEQUENCE: 29

```
Val Tyr Ser Phe Leu Tyr Val Leu Val Ile Val Arg Lys Leu Leu Ser
1               5                   10                  15

Met Lys Lys Arg Ile Glu Arg Leu
            20
```

<210> SEQ ID NO 30
<211> LENGTH: 18
<212> TYPE: PRT
<213> ORGANISM: Artificial
<220> FEATURE:
<223> OTHER INFORMATION: Antimicrobial peptide and/or targeting peptide

<400> SEQUENCE: 30

```
Gly Ile Val Leu Ile Gly Leu Lys Leu Ile Pro Leu Leu Ala Asn Val
1               5                   10                  15

Leu Arg
```

<210> SEQ ID NO 31
<211> LENGTH: 21
<212> TYPE: PRT
<213> ORGANISM: Artificial
<220> FEATURE:
<223> OTHER INFORMATION: Antimicrobial peptide and/or targeting peptide

<400> SEQUENCE: 31

```
Val Met Gln Ser Leu Tyr Val Lys Pro Pro Leu Ile Leu Val Thr Lys
```

-continued

```
                1               5                  10                  15

Leu Ala Gln Gln Asn
            20

<210> SEQ ID NO 32
<211> LENGTH: 16
<212> TYPE: PRT
<213> ORGANISM: Artificial
<220> FEATURE:
<223> OTHER INFORMATION: Antimicrobial peptide and/or targeting peptide

<400> SEQUENCE: 32

Ser Phe Met Pro Glu Ile Gln Lys Asn Thr Ile Pro Thr Gln Met Lys
1               5                   10                  15

<210> SEQ ID NO 33
<211> LENGTH: 39
<212> TYPE: PRT
<213> ORGANISM: Artificial
<220> FEATURE:
<223> OTHER INFORMATION: Antimicrobial peptide and/or targeting peptide

<400> SEQUENCE: 33

Leu Gly Leu Thr Ala Gly Val Ala Tyr Ala Ala Gln Pro Thr Asn Gln
1               5                   10                  15

Pro Thr Asn Gln Pro Thr Asn Gln Pro Thr Asn Gln Pro Thr Asn Gln
            20                  25                  30

Pro Thr Asn Gln Pro Arg Trp
        35

<210> SEQ ID NO 34
<211> LENGTH: 15
<212> TYPE: PRT
<213> ORGANISM: Artificial
<220> FEATURE:
<223> OTHER INFORMATION: Antimicrobial peptide and/or targeting peptide

<400> SEQUENCE: 34

Cys Gly Lys Leu Leu Glu Gln Lys Asn Phe Phe Leu Lys Thr Arg
1               5                   10                  15

<210> SEQ ID NO 35
<211> LENGTH: 30
<212> TYPE: PRT
<213> ORGANISM: Artificial
<220> FEATURE:
<223> OTHER INFORMATION: Antimicrobial peptide and/or targeting peptide

<400> SEQUENCE: 35

Ala Ser Lys Gln Ala Ser Lys Gln Ala Ser Lys Gln Ala Ser Lys Gln
1               5                   10                  15

Ala Ser Lys Gln Ala Ser Arg Ser Leu Lys Asn His Leu Leu
            20                  25                  30

<210> SEQ ID NO 36
<211> LENGTH: 24
<212> TYPE: PRT
<213> ORGANISM: Artificial
<220> FEATURE:
<223> OTHER INFORMATION: Antimicrobial peptide and/or targeting peptide

<400> SEQUENCE: 36

Pro Asp Ala Pro Arg Thr Cys Tyr His Lys Pro Ile Leu Ala Ala Leu
1               5                   10                  15

Ser Arg Ile Val Val Thr Asp Arg
```

20

<210> SEQ ID NO 37
<211> LENGTH: 8
<212> TYPE: PRT
<213> ORGANISM: Artificial
<220> FEATURE:
<223> OTHER INFORMATION: Antimicrobial peptide and/or targeting peptide

<400> SEQUENCE: 37

Asn Tyr Ala Val Val Ser His Thr
1               5

<210> SEQ ID NO 38
<211> LENGTH: 17
<212> TYPE: PRT
<213> ORGANISM: Artificial
<220> FEATURE:
<223> OTHER INFORMATION: Antimicrobial peptide and/or targeting peptide

<400> SEQUENCE: 38

Ile Leu Val Leu Leu Ala Leu Gln Val Glu Leu Asp Ser Lys Phe Gln
1               5                   10                  15

Tyr

<210> SEQ ID NO 39
<211> LENGTH: 12
<212> TYPE: PRT
<213> ORGANISM: Artificial
<220> FEATURE:
<223> OTHER INFORMATION: Antimicrobial peptide and/or targeting peptide

<400> SEQUENCE: 39

Tyr Val Asn Tyr Asn Gln Ser Phe Asn Ser Gly Trp
1               5                   10

<210> SEQ ID NO 40
<211> LENGTH: 23
<212> TYPE: PRT
<213> ORGANISM: Artificial
<220> FEATURE:
<223> OTHER INFORMATION: Antimicrobial peptide and/or targeting peptide

<400> SEQUENCE: 40

Phe Gln Lys Pro Phe Thr Gly Glu Glu Val Glu Asp Phe Gln Asp Asp
1               5                   10                  15

Asp Glu Ile Pro Thr Ile Ile
            20

<210> SEQ ID NO 41
<211> LENGTH: 4
<212> TYPE: PRT
<213> ORGANISM: Artificial
<220> FEATURE:
<223> OTHER INFORMATION: Peptide linker

<400> SEQUENCE: 41

Gly Gly Gly Gly
1

<210> SEQ ID NO 42
<211> LENGTH: 5
<212> TYPE: PRT
<213> ORGANISM: Artificial
<220> FEATURE:
<223> OTHER INFORMATION: Peptide linker

```
<400> SEQUENCE: 42

Gly Gly Gly Gly Gly
1               5

<210> SEQ ID NO 43
<211> LENGTH: 6
<212> TYPE: PRT
<213> ORGANISM: Artificial
<220> FEATURE:
<223> OTHER INFORMATION: Peptide linker

<400> SEQUENCE: 43

Gly Gly Ser Gly Gly Ser
1               5

<210> SEQ ID NO 44
<211> LENGTH: 5
<212> TYPE: PRT
<213> ORGANISM: Artificial
<220> FEATURE:
<223> OTHER INFORMATION: Peptide linker

<400> SEQUENCE: 44

Pro Ser Pro Ser Pro
1               5

<210> SEQ ID NO 45
<211> LENGTH: 5
<212> TYPE: PRT
<213> ORGANISM: Artificial
<220> FEATURE:
<223> OTHER INFORMATION: Peptide linker

<400> SEQUENCE: 45

Ala Ser Ala Ser Ala
1               5

<210> SEQ ID NO 46
<211> LENGTH: 5
<212> TYPE: PRT
<213> ORGANISM: Artificial
<220> FEATURE:
<223> OTHER INFORMATION: Peptide linker

<400> SEQUENCE: 46

Pro Ser Pro Ser Pro
1               5

<210> SEQ ID NO 47
<211> LENGTH: 4
<212> TYPE: PRT
<213> ORGANISM: Artificial
<220> FEATURE:
<223> OTHER INFORMATION: Peptide linker

<400> SEQUENCE: 47

Lys Lys Lys Lys
1

<210> SEQ ID NO 48
<211> LENGTH: 4
<212> TYPE: PRT
<213> ORGANISM: Artificial
<220> FEATURE:
<223> OTHER INFORMATION: Peptide linker

<400> SEQUENCE: 48
```

```
Arg Arg Arg Arg
1

<210> SEQ ID NO 49
<211> LENGTH: 5
<212> TYPE: PRT
<213> ORGANISM: Artificial
<220> FEATURE:
<223> OTHER INFORMATION: Peptide linker

<400> SEQUENCE: 49

Gly Gly Gly Gly Ser
1               5

<210> SEQ ID NO 50
<211> LENGTH: 10
<212> TYPE: PRT
<213> ORGANISM: Artificial
<220> FEATURE:
<223> OTHER INFORMATION: Peptide linker

<400> SEQUENCE: 50

Gly Gly Gly Gly Ser Gly Gly Gly Gly Ser
1               5                   10

<210> SEQ ID NO 51
<211> LENGTH: 15
<212> TYPE: PRT
<213> ORGANISM: Artificial
<220> FEATURE:
<223> OTHER INFORMATION: Peptide linker

<400> SEQUENCE: 51

Gly Gly Gly Gly Ser Gly Gly Gly Gly Ser Gly Gly Gly Gly Ser
1               5                   10                  15

<210> SEQ ID NO 52
<211> LENGTH: 20
<212> TYPE: PRT
<213> ORGANISM: Artificial
<220> FEATURE:
<223> OTHER INFORMATION: Peptide linker

<400> SEQUENCE: 52

Gly Gly Gly Gly Ser Gly Gly Gly Gly Ser Gly Gly Gly Gly Ser Gly
1               5                   10                  15

Gly Gly Gly Ser
            20

<210> SEQ ID NO 53
<211> LENGTH: 25
<212> TYPE: PRT
<213> ORGANISM: Artificial
<220> FEATURE:
<223> OTHER INFORMATION: Peptide linker

<400> SEQUENCE: 53

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 54
<211> LENGTH: 30
<212> TYPE: PRT
<213> ORGANISM: Artificial
<220> FEATURE:
```

```
<223> OTHER INFORMATION: Peptide linker

<400> SEQUENCE: 54

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser
            20                  25                  30

<210> SEQ ID NO 55
<211> LENGTH: 16
<212> TYPE: PRT
<213> ORGANISM: Artificial
<220> FEATURE:
<223> OTHER INFORMATION: Antimicrobial peptide and/or targeting peptide

<400> SEQUENCE: 55

Thr Phe Phe Arg Leu Phe Asn Arg Ser Phe Thr Gln Ala Leu Gly Lys
1               5                   10                  15

<210> SEQ ID NO 56
<211> LENGTH: 8
<212> TYPE: PRT
<213> ORGANISM: Artificial
<220> FEATURE:
<223> OTHER INFORMATION: Antimicrobial peptide and/or targeting peptide

<400> SEQUENCE: 56

Thr Phe Phe Arg Leu Phe Asn Arg
1               5

<210> SEQ ID NO 57
<211> LENGTH: 8
<212> TYPE: PRT
<213> ORGANISM: Artificial
<220> FEATURE:
<223> OTHER INFORMATION: Antimicrobial peptide and/or targeting peptide

<400> SEQUENCE: 57

Asn Ile Phe Glu Tyr Phe Leu Glu
1               5

<210> SEQ ID NO 58
<211> LENGTH: 15
<212> TYPE: PRT
<213> ORGANISM: Artificial
<220> FEATURE:
<223> OTHER INFORMATION: Antimicrobial peptide and/or targeting peptide

<400> SEQUENCE: 58

Lys Phe Ile Asn Gly Val Leu Ser Gln Phe Val Leu Glu Arg Lys
1               5                   10                  15

<210> SEQ ID NO 59
<211> LENGTH: 9
<212> TYPE: PRT
<213> ORGANISM: Artificial
<220> FEATURE:
<223> OTHER INFORMATION: Antimicrobial peptide and/or targeting peptide

<400> SEQUENCE: 59

Tyr Ser Lys Thr Leu His Phe Ala Asp
1               5

<210> SEQ ID NO 60
<211> LENGTH: 27
<212> TYPE: PRT
<213> ORGANISM: Artificial
```

```
<220> FEATURE:
<223> OTHER INFORMATION: Antimicrobial peptide and/or targeting peptide

<400> SEQUENCE: 60

Gly Lys Ala Lys Pro Tyr Gln Val Arg Gln Val Leu Arg Ala Val Asp
1               5                   10                  15

Lys Leu Glu Thr Arg Arg Lys Lys Gly Gly Arg
            20                  25

<210> SEQ ID NO 61
<211> LENGTH: 23
<212> TYPE: PRT
<213> ORGANISM: Artificial
<220> FEATURE:
<223> OTHER INFORMATION: Antimicrobial peptide and/or targeting peptide

<400> SEQUENCE: 61

Ser Lys Arg Gly Arg Lys Arg Lys Asp Arg Arg Lys Lys Lys Ala Asn
1               5                   10                  15

His Gly Lys Arg Pro Asn Ser
            20

<210> SEQ ID NO 62
<211> LENGTH: 5
<212> TYPE: PRT
<213> ORGANISM: Artificial
<220> FEATURE:
<223> OTHER INFORMATION: Antimicrobial peptide and/or targeting peptide

<400> SEQUENCE: 62

His Ser Ser His Leu
1               5

<210> SEQ ID NO 63
<211> LENGTH: 6
<212> TYPE: PRT
<213> ORGANISM: Artificial
<220> FEATURE:
<223> OTHER INFORMATION: Antimicrobial peptide and/or targeting peptide

<400> SEQUENCE: 63

Asp Leu Arg Lys Ala Lys
1               5

<210> SEQ ID NO 64
<211> LENGTH: 5
<212> TYPE: PRT
<213> ORGANISM: Artificial
<220> FEATURE:
<223> OTHER INFORMATION: Antimicrobial peptide and/or targeting peptide

<400> SEQUENCE: 64

Leu Val Arg Leu Ala
1               5

<210> SEQ ID NO 65
<211> LENGTH: 17
<212> TYPE: PRT
<213> ORGANISM: Artificial
<220> FEATURE:
<223> OTHER INFORMATION: Antimicrobial peptide and/or targeting peptide

<400> SEQUENCE: 65

Glu Val Tyr Ser Ser Pro Thr Asn Asn Val Ala Ile Thr Val Gln Asn
1               5                   10                  15

Asn
```

-continued

```
<210> SEQ ID NO 66
<211> LENGTH: 32
<212> TYPE: PRT
<213> ORGANISM: Artificial
<220> FEATURE:
<223> OTHER INFORMATION: Antimicrobial peptide and/or targeting peptide

<400> SEQUENCE: 66

Ser Lys Phe Glu Leu Val Asn Tyr Ala Ser Gly Cys Ser Cys Gly Ala
1               5                   10                  15

Asp Cys Lys Cys Ala Ser Glu Thr Glu Cys Lys Cys Ala Ser Lys Lys
            20                  25                  30

<210> SEQ ID NO 67
<211> LENGTH: 28
<212> TYPE: PRT
<213> ORGANISM: Artificial
<220> FEATURE:
<223> OTHER INFORMATION: Antimicrobial peptide and/or targeting peptide

<400> SEQUENCE: 67

Gly Val Gly Ile Gly Phe Ile Met Met Gly Val Val Gly Tyr Ala Val
1               5                   10                  15

Lys Leu Val His Ile Pro Ile Arg Tyr Leu Ile Val
            20                  25

<210> SEQ ID NO 68
<211> LENGTH: 27
<212> TYPE: PRT
<213> ORGANISM: Artificial
<220> FEATURE:
<223> OTHER INFORMATION: Antimicrobial peptide and/or targeting peptide

<400> SEQUENCE: 68

His Ala Arg Ala Ala Val Gly Val Ala Glu Leu Pro Arg Gly Ala Ala
1               5                   10                  15

Val Glu Val Glu Leu Ile Ala Ala Val Arg Pro
            20                  25

<210> SEQ ID NO 69
<211> LENGTH: 8
<212> TYPE: PRT
<213> ORGANISM: Artificial
<220> FEATURE:
<223> OTHER INFORMATION: Antimicrobial peptide and/or targeting peptide

<400> SEQUENCE: 69

Val Val Arg Arg Phe Gln Gly Met
1               5

<210> SEQ ID NO 70
<211> LENGTH: 26
<212> TYPE: PRT
<213> ORGANISM: Artificial
<220> FEATURE:
<223> OTHER INFORMATION: Antimicrobial peptide and/or targeting peptide

<400> SEQUENCE: 70

Asn Ile Leu Phe Gly Ile Ile Gly Phe Val Val Ala Met Thr Ala Ala
1               5                   10                  15

Val Ile Val Thr Ala Ile Ser Ile Ala Lys
            20                  25

<210> SEQ ID NO 71
```

-continued

```
<211> LENGTH: 30
<212> TYPE: PRT
<213> ORGANISM: Artificial
<220> FEATURE:
<223> OTHER INFORMATION: Antimicrobial peptide and/or targeting peptide

<400> SEQUENCE: 71

Met Pro Lys Ala Arg Pro Val Asn His Asn Lys Lys Ser Lys Ile
1               5                   10                  15

Thr Ile Lys Ser Asn Phe Thr Leu Phe Tyr Met Phe Asn Pro
            20                  25                  30

<210> SEQ ID NO 72
<211> LENGTH: 30
<212> TYPE: PRT
<213> ORGANISM: Artificial
<220> FEATURE:
<223> OTHER INFORMATION: Antimicrobial peptide and/or targeting peptide

<400> SEQUENCE: 72

Met Ile His Leu Thr Lys Gln Asn Thr Met Glu Ala Leu His Phe Ile
1               5                   10                  15

Lys Gln Phe Tyr Asp Met Phe Phe Ile Leu Asn Phe Asn Val
            20                  25                  30

<210> SEQ ID NO 73
<211> LENGTH: 25
<212> TYPE: PRT
<213> ORGANISM: Artificial
<220> FEATURE:
<223> OTHER INFORMATION: Antimicrobial peptide and/or targeting peptide

<400> SEQUENCE: 73

Arg Phe Phe Asn Phe Glu Ile Lys Lys Ser Thr Lys Val Asp Tyr Val
1               5                   10                  15

Phe Ala His Val Asp Leu Ser Asp Val
            20                  25

<210> SEQ ID NO 74
<211> LENGTH: 33
<212> TYPE: PRT
<213> ORGANISM: Artificial
<220> FEATURE:
<223> OTHER INFORMATION: Antimicrobial peptide and/or targeting peptide

<400> SEQUENCE: 74

Glu Ile Leu Asn Asn Asn Gln Val Ile Lys Glu Leu Thr Met Lys Tyr
1               5                   10                  15

Lys Thr Gln Phe Glu Ser Asn Leu Gly Gly Trp Thr Ala Arg Ala Arg
            20                  25                  30

Arg

<210> SEQ ID NO 75
<211> LENGTH: 28
<212> TYPE: PRT
<213> ORGANISM: Artificial
<220> FEATURE:
<223> OTHER INFORMATION: Antimicrobial peptide and/or targeting peptide

<400> SEQUENCE: 75

Lys Phe Gln Gly Glu Phe Thr Asn Ile Gly Gln Ser Tyr Ile Val Ser
1               5                   10                  15

Ala Ser His Met Ser Thr Ser Leu Asn Thr Gly Lys
            20                  25
```

<210> SEQ ID NO 76
<211> LENGTH: 20
<212> TYPE: PRT
<213> ORGANISM: Artificial
<220> FEATURE:
<223> OTHER INFORMATION: Antimicrobial peptide and/or targeting peptide

<400> SEQUENCE: 76

Val Tyr Arg His Leu Arg Phe Ile Asp Gly Lys Leu Val Glu Ile Arg
1               5                   10                  15

Leu Glu Arg Lys
            20

<210> SEQ ID NO 77
<211> LENGTH: 24
<212> TYPE: PRT
<213> ORGANISM: Artificial
<220> FEATURE:
<223> OTHER INFORMATION: Antimicrobial peptide and/or targeting peptide

<400> SEQUENCE: 77

Lys Leu Arg Ser Ala Ser Lys Lys Ser Leu Gln Glu Lys Ser Cys Gly
1               5                   10                  15

Ile Met Pro Glu Lys Pro Ala Gly
            20

<210> SEQ ID NO 78
<211> LENGTH: 20
<212> TYPE: PRT
<213> ORGANISM: Artificial
<220> FEATURE:
<223> OTHER INFORMATION: Antimicrobial peptide and/or targeting peptide

<400> SEQUENCE: 78

Phe Arg Ser Pro Cys Ile Asn Asn Ser Leu Gln Pro Pro Gly Val
1               5                   10                  15

Tyr Pro Ala Arg
            20

<210> SEQ ID NO 79
<211> LENGTH: 30
<212> TYPE: PRT
<213> ORGANISM: Artificial
<220> FEATURE:
<223> OTHER INFORMATION: Antimicrobial peptide and/or targeting peptide

<400> SEQUENCE: 79

Tyr Val Glu Glu Ala Val Arg Ala Ala Leu Lys Lys Glu Ala Arg Ile
1               5                   10                  15

Ser Thr Glu Asp Thr Pro Val Asn Leu Pro Ser Phe Asp Cys
            20                  25                  30

<210> SEQ ID NO 80
<211> LENGTH: 16
<212> TYPE: PRT
<213> ORGANISM: Artificial
<220> FEATURE:
<223> OTHER INFORMATION: Antimicrobial peptide and/or targeting peptide

<400> SEQUENCE: 80

Met Thr Cys His Gln Ala Pro Thr Thr Thr His Gln Ser Asn Met Ala
1               5                   10                  15

<210> SEQ ID NO 81
<211> LENGTH: 30

```
<212> TYPE: PRT
<213> ORGANISM: Artificial
<220> FEATURE:
<223> OTHER INFORMATION: Antimicrobial peptide and/or targeting peptide

<400> SEQUENCE: 81

Met Val Ile Leu Val Phe Ser Leu Ile Phe Ile Phe Thr Asp Asn Tyr
1               5                   10                  15

Leu Val Tyr Gln Ser Lys Ser Ile Lys Glu Asp Val Met Ile
            20                  25                  30

<210> SEQ ID NO 82
<211> LENGTH: 16
<212> TYPE: PRT
<213> ORGANISM: Artificial
<220> FEATURE:
<223> OTHER INFORMATION: Antimicrobial peptide and/or targeting peptide

<400> SEQUENCE: 82

Lys Lys Ile Ile Pro Leu Ile Thr Leu Phe Val Val Thr Leu Val Gly
1               5                   10                  15

<210> SEQ ID NO 83
<211> LENGTH: 21
<212> TYPE: PRT
<213> ORGANISM: Artificial
<220> FEATURE:
<223> OTHER INFORMATION: Antimicrobial peptide and/or targeting peptide

<400> SEQUENCE: 83

Asp Lys Ser Thr Gln Asp Lys Asp Ile Lys Gln Ala Lys Leu Leu Ala
1               5                   10                  15

Gln Glu Leu Gly Leu
            20

<210> SEQ ID NO 84
<211> LENGTH: 25
<212> TYPE: PRT
<213> ORGANISM: Artificial
<220> FEATURE:
<223> OTHER INFORMATION: Antimicrobial peptide and/or targeting peptide

<400> SEQUENCE: 84

Ile Ser Leu Ile Ile Phe Ile Met Leu Phe Val Val Ala Leu Phe Lys
1               5                   10                  15

Cys Ile Thr Asn Tyr Lys His Gln Ser
            20                  25

<210> SEQ ID NO 85
<211> LENGTH: 10
<212> TYPE: PRT
<213> ORGANISM: Artificial
<220> FEATURE:
<223> OTHER INFORMATION: Antimicrobial peptide and/or targeting peptide

<400> SEQUENCE: 85

Gly Met Pro Gln Ile Pro Arg Leu Arg Ile
1               5                   10

<210> SEQ ID NO 86
<211> LENGTH: 4
<212> TYPE: PRT
<213> ORGANISM: Artificial
<220> FEATURE:
<223> OTHER INFORMATION: Antimicrobial peptide and/or targeting peptide

<400> SEQUENCE: 86
```

```
Ile Asp Met Arg
1

<210> SEQ ID NO 87
<211> LENGTH: 26
<212> TYPE: PRT
<213> ORGANISM: Artificial
<220> FEATURE:
<223> OTHER INFORMATION: Antimicrobial peptide and/or targeting peptide

<400> SEQUENCE: 87

Asp Ser Phe Asp Ser Leu Ser Pro Phe Arg Glu Arg Gly Gly Glu Arg
1               5                   10                  15

Glu Asp Gly Cys Asp Ala Met Pro Leu Pro
            20                  25

<210> SEQ ID NO 88
<211> LENGTH: 5
<212> TYPE: PRT
<213> ORGANISM: Artificial
<220> FEATURE:
<223> OTHER INFORMATION: Antimicrobial peptide and/or targeting peptide

<400> SEQUENCE: 88

Asn Asp Asp Ala Gln
1               5

<210> SEQ ID NO 89
<211> LENGTH: 32
<212> TYPE: PRT
<213> ORGANISM: Artificial
<220> FEATURE:
<223> OTHER INFORMATION: Antimicrobial peptide and/or targeting peptide

<400> SEQUENCE: 89

Ala Leu Ala Leu Leu Lys Gln Asp Leu Leu Asn Phe Glu Gly Arg Gly
1               5                   10                  15

Arg Ile Ile Thr Ser Thr Tyr Leu Gln Phe Asn Glu Gly Cys Val Pro
            20                  25                  30

<210> SEQ ID NO 90
<211> LENGTH: 14
<212> TYPE: PRT
<213> ORGANISM: Artificial
<220> FEATURE:
<223> OTHER INFORMATION: Antimicrobial peptide and/or targeting peptide

<400> SEQUENCE: 90

Phe Ser Leu Asn Phe Ser Lys Gln Lys Tyr Val Thr Val Asn
1               5                   10

<210> SEQ ID NO 91
<211> LENGTH: 12
<212> TYPE: PRT
<213> ORGANISM: Artificial
<220> FEATURE:
<223> OTHER INFORMATION: Antimicrobial peptide and/or targeting peptide

<400> SEQUENCE: 91

Ala Leu Ala Gly Leu Ala Gly Leu Ile Ser Gly Lys
1               5                   10

<210> SEQ ID NO 92
<211> LENGTH: 9
<212> TYPE: PRT
<213> ORGANISM: Artificial
```

```
<220> FEATURE:
<223> OTHER INFORMATION: Antimicrobial peptide and/or targeting peptide

<400> SEQUENCE: 92

Asp Val Ile Leu Arg Val Glu Ala Gln
1               5

<210> SEQ ID NO 93
<211> LENGTH: 12
<212> TYPE: PRT
<213> ORGANISM: Artificial
<220> FEATURE:
<223> OTHER INFORMATION: Antimicrobial peptide and/or targeting peptide

<400> SEQUENCE: 93

Gly Leu Ala Ala Ile Ala Thr Val Phe Ala Leu Tyr
1               5                   10

<210> SEQ ID NO 94
<211> LENGTH: 8
<212> TYPE: PRT
<213> ORGANISM: Artificial
<220> FEATURE:
<223> OTHER INFORMATION: Antimicrobial peptide and/or targeting peptide

<400> SEQUENCE: 94

Pro Met Asn Ala Ala Glu Pro Glu
1               5

<210> SEQ ID NO 95
<211> LENGTH: 7
<212> TYPE: PRT
<213> ORGANISM: Artificial
<220> FEATURE:
<223> OTHER INFORMATION: Antimicrobial peptide and/or targeting peptide

<400> SEQUENCE: 95

Pro Pro Ser Ser Phe Leu Val
1               5

<210> SEQ ID NO 96
<211> LENGTH: 18
<212> TYPE: PRT
<213> ORGANISM: Artificial
<220> FEATURE:
<223> OTHER INFORMATION: Antimicrobial peptide and/or targeting peptide

<400> SEQUENCE: 96

Leu Ile Ile Tyr Phe Ser Lys Thr Gly Asn Thr Ala Arg Ala Thr Arg
1               5                   10                  15

Gln Ile

<210> SEQ ID NO 97
<211> LENGTH: 13
<212> TYPE: PRT
<213> ORGANISM: Artificial
<220> FEATURE:
<223> OTHER INFORMATION: Antimicrobial peptide and/or targeting peptide

<400> SEQUENCE: 97

Ser Lys Lys Tyr Asn His Ile Leu Asn Gln Glu Asn Arg
1               5                   10

<210> SEQ ID NO 98
<211> LENGTH: 8
<212> TYPE: PRT
<213> ORGANISM: Artificial
```

```
<220> FEATURE:
<223> OTHER INFORMATION: Antimicrobial peptide and/or targeting peptide

<400> SEQUENCE: 98

Asn Asn Ala Ile Val Tyr Ile Ser
1               5

<210> SEQ ID NO 99
<211> LENGTH: 20
<212> TYPE: PRT
<213> ORGANISM: Artificial
<220> FEATURE:
<223> OTHER INFORMATION: Antimicrobial peptide and/or targeting peptide

<400> SEQUENCE: 99

Pro Ala Leu Val Asp Leu Ser Asn Lys Glu Ala Val Trp Ala Val Leu
1               5                   10                  15

Asp Asp His Ser
            20

<210> SEQ ID NO 100
<211> LENGTH: 11
<212> TYPE: PRT
<213> ORGANISM: Artificial
<220> FEATURE:
<223> OTHER INFORMATION: Antimicrobial peptide and/or targeting peptide

<400> SEQUENCE: 100

Gly Gly Thr Lys Glu Ile Val Tyr Gln Arg Gly
1               5                   10

<210> SEQ ID NO 101
<211> LENGTH: 15
<212> TYPE: PRT
<213> ORGANISM: Artificial
<220> FEATURE:
<223> OTHER INFORMATION: Antimicrobial peptide and/or targeting peptide

<400> SEQUENCE: 101

Asn Arg Gln Ala Gln Gly Glu Arg Ala His Gly Glu Gln Gln Gly
1               5                   10                  15

<210> SEQ ID NO 102
<211> LENGTH: 20
<212> TYPE: PRT
<213> ORGANISM: Artificial
<220> FEATURE:
<223> OTHER INFORMATION: Antimicrobial peptide and/or targeting peptide

<400> SEQUENCE: 102

Ala Ile Glu Gly Val Ile Lys Lys Gly Ala Cys Phe Lys Leu Leu Arg
1               5                   10                  15

His Glu Met Phe
            20

<210> SEQ ID NO 103
<211> LENGTH: 28
<212> TYPE: PRT
<213> ORGANISM: Artificial
<220> FEATURE:
<223> OTHER INFORMATION: Antimicrobial peptide and/or targeting peptide

<400> SEQUENCE: 103

Val Leu Pro Phe Pro Ala Ile Pro Leu Ser Arg Arg Arg Ala Cys Val
1               5                   10                  15

Ala Ala Pro Arg Pro Arg Ser Arg Gln Arg Ala Ser
```

```
<210> SEQ ID NO 104
<211> LENGTH: 15
<212> TYPE: PRT
<213> ORGANISM: Artificial
<220> FEATURE:
<223> OTHER INFORMATION: Antimicrobial peptide and/or targeting peptide

<400> SEQUENCE: 104

Arg Leu Ala Arg Gly Arg Pro Thr Asn Leu Cys Gly Arg Arg Gly
1               5                   10                  15

<210> SEQ ID NO 105
<211> LENGTH: 19
<212> TYPE: PRT
<213> ORGANISM: Artificial
<220> FEATURE:
<223> OTHER INFORMATION: Antimicrobial peptide and/or targeting peptide

<400> SEQUENCE: 105

Arg Leu Thr Ser Asn Gln Phe Leu Thr Arg Ile Thr Pro Phe Val Phe
1               5                   10                  15

Ala Gln His
```

ANTIBACTERIAL AND ANTIFUNGAL PEPTIDES

CROSS-REFERENCE TO RELATED APPLICATIONS

This application claims benefit of and priority to U.S. Ser. No. 61/142,830, filed Jan. 6, 2009, U.S. Ser. No. 61/151,445, filed Feb. 10, 2009, U.S. Ser. No. 61/243,905, filed Sep. 18, 2009, and U.S. Ser. No. 61/243,930, filed Sep. 18, 2009, all of which are incorporated herein by reference in their entirety for all purposes.

STATEMENT OF GOVERNMENTAL SUPPORT

[Not Applicable]

FIELD OF THE INVENTION

The present invention relates to the fields of antibiotics and pharmacology. More particularly this invention pertains to the identification of novel antimicrobial peptides (AMPs) that have activity against a number of bacteria and/or fungi.

BACKGROUND OF THE INVENTION

The development of antimicrobial agents led to a significant decrease in morbidity and mortality from infectious diseases in this century. This accomplishment was largely due to the widespread use of the major classes of antibiotics, such as the sulfonamides, penicillins, cephalosporins, aminoglycosides, and tetracyclines (see, e.g., Goodman et al. (1995) *The Pharmacological Basis of Therapeutics*, Macmillan Publishing, New York). However, in recent years, the trend in reducing infectious disease mortality has been threatened by the emergence of resistant strains of microorganisms that are no longer susceptible to the currently available antimicrobial agents.

With the rise of antibiotic-resistant pathogens and infectious diseases, the need for new antimicrobial agents is urgent (see, e.g., Cohen et al. (1992) *Science* 257: 1050-1055). For example, the incidence of community-acquired and nosocomially acquired infections due to the bacterium *Staphylococcus aureus* is rising (Lowy (1998) *N. Engl. J. Med.* 339: 520-532.). From 1990 to 1992, this microorganism was the most common cause of nosocomial pneumonias and surgical wound infections (Emori and Gaynes (1993) *Clin. Microbiol. Rev.* 23: 255-259). The overall growing crisis in antibiotic resistance and the rise in the incidence of methicillin-resistant *S. aureus* (MRSA) strains (Schwarz et al. (1981) *Mol. Gen. Genet.* 183:181-186; Sista et al. (2004) *Anesthesiol. Clin. N. Am.* 22: 405-435.) have emphasized the need for therapeutic alternatives to currently available antibiotics. Vancomycin remains the mainstay of therapy against several resistant gram-positive pathogens. However, vancomycin is slowly bactericidal, and with the recent increase in nosocomial infections caused by vancomycin-resistant enterococci and *S. aureus* (Centers for Disease Control and Prevention (2002) *Morbid. Mortal. Wkly. Rep.* 51: 565-567; Diekema et al. (2004) *Clin. Infect. Dis.* 38: 78-85; Fujimura et al. (2004) *J. Infect. Chemother.*, 10: 131-132), there is a growing need for antimicrobial agents with novel mechanisms of action to attack these resistant pathogens.

Biologically active peptides, such as antimicrobial peptides (hereinafter "AMPs"), are believed to be less likely to develop resistance because the antimicrobial peptides show activity by mechanisms that are totally different from that of conventional antibiotics.

Typically AMPs are low molecular weight peptides that exhibit antimicrobial activity. Naturally-occurring AMPs are part of the innate immune response of plants, invertebrates and vertebrates. AMPs include, among others, cecropins (see, e.g., Hultmark et al. (1980) *Eur. J. Biochem.*, 106: 7-16; Hultmark et al. (1982) *Eur. J. Biochem.*, 127: 207-217), apidaecins (see, e.g., Casteels et al. (1989) *EMBO J.* 8: 2387-2391), magainins (see, e.g., Zasloff (1987) *Proc. Natl. Acad. Sci., USA*, 84: 5449-5453; Zasloff et al. (1988) *Proc. Natl. Acad. Sci., USA*, 85: 910-913), tachyplesins and analogues of tachyplesins such as polyphemusins (see, e.g., Nakamura et al. (1988) *J. Biol. Chem.* 263: 16709-16713; Miyata et al. (1989) *J. Biochem.*, 106: 663-668), defensins (Lehrer et al. (1991) *Cell* 64: 229-230; Lehrer et al. (1993) *Ann. Rev. Immunol.*, 11: 105-128; U.S. Pat. Nos. 4,705,777; 4,659,692; 4,543,252), β-defensins (see, e.g., Selsted et al. (1993) *J. Biol. Chem.*, 288: 6641-6648; Diamond et al. (1991) *Proc. Natl. Acad. Sci., USA*, 88: 3952-3958), insect defensins (see, e.g., Lambert et al. (1989) *Proc. Natl. Acad. Sci., USA*, 88: 262-265; Matsuyama and Natori (1988) *J. Biol. Chem.*, 263: 17112-17116), and protegrins (see, e.g., Kokryakov et al. (1993) *FEBS* 337: 231-236; Zhao et al. (1994) *FEBS Lett.* 346: 285-288; Migorodskaya et al. (1993) *FEBS* 330: 339-342; Storici et al. (1993) *Biochem. Biophys. Res. Commun.*, 196: 1363-1367; Zhao et al. (1994) *FEBS Lett.* 346: 285-288; Manzoni et al. (1996) *FEBS Lett.* 383: 93-98; U.S. Pat. No. 5,464,823). The discovery of these new classes of antimicrobial peptides offers hope that some might be developed into agents that can be used against microorganisms of medicinal importance.

At least one antimicrobial peptide, daptomycin, a cyclic lipodepsipeptide antibiotic, has been approved for the treatment of complicated skin and skin structure infections caused by several gram-positive bacteria. Its mode of action appears to be related to the disruption of the membrane potential of the bacterium, which is caused by the favored oligomerization of daptomycin upon extracellular calcium binding (Jeu and Fung (2004) *Clin. Ther.* 26: 1728-1757).

SUMMARY OF THE INVENTION

In various embodiments novel antimicrobial peptides (AMPs) are provided. The peptides are useful in a variety of contexts including, but not limited to pharmaceuticals, and topical disinfectants.

Accordingly, certain embodiments provide an isolated antimicrobial peptide having antimicrobial activity against at least one kind of bacteria, fungus, or yeast, the antimicrobial peptide ranging in length up to about 80, about 70, or about 60 amino acids and comprising an amino acid sequence selected from group consisting of GSVIKKRRKRMSKKKHRKML-RRTRVQRRKLGK (PF-S028, SEQ ID NO:1), NYR-LVNAIFSKIFKKKFIKF (PF-C252, SEQ ID NO:2), YIQF-HLNQQPRPKVKKIKIFL (PF-531, SEQ ID NO:3), GSVIKKRRKRMAKKKHRKLLKKTRIQRRRAGK (PF-527, SEQ ID NO:4), MRFGSLALVAYDSAIKHSWPRPSS-VRRLRM (PF-672, SEQ ID NO:5), FESKILNASKELD-KEKKVNTALSFNSHQDFAKAYQNGKI (PF-606, SEQ ID NO:6), KGKSLMPLLKQINQWGKLYL (PF-C239, SEQ ID NO:7), WSRVPGHSDTGWKVWHRW (PF-547, SEQ ID NO:8), MGIIAGIIKFIKGLIEKFTGK (PF-006, SEQ ID NO:9), ILNKKPKLPLWKLGKNYFRRFYVLPTFLA (PF-C287, SEQ ID NO:10), RESKLIAMADMIRRRI (PF-545, SEQ ID NO:11), LDPLEPRIAPPGDRSHQGAPACHRD- PLRGRSARDAER (PF-C019, SEQ ID NO:12), MPVSKKRYMLSSAYATALGICYGQVAT-DEKESEITAIPDLLDYLSVEEYLL (PF-C163, SEQ ID NO:13), LSLATFAKIFMTRSNWSLKRFNRL (PF-278, SEQ ID NO:14), MIRIRSPTKKKLNRNSISDWKSNTS-GRFFY (PF-283, SEQ ID NO:15), MKRRRCNWCGKL-FYLEEKSKEAYCCKECRKKAKKVKK (PF-307, SEQ ID NO:16), VLPFPAIPLSRRRACVAAPRPRSRQRAS (PF-168, SEQ ID NO:17), KNKKQTDILEKVKEILDKKKK-TKSVGQKLY (PF-538, SEQ ID NO:18), SLQSQLGPCLH-DQRH (PF-448, SEQ ID NO:19), WKRLWPARILAGHSRRRMRWMVVWRYFAAT (PF-C021, SEQ ID NO:20), KFQGEFT-NIGQSYIVSASHMSTSLNTGK (PF-583, SEQ ID NO:21), TKKIELKRFVDAFVKKSYENYILER-ELKKLIKAINEELPTK (PF-600, SEQ ID NO:22), KFSD-QIDKGQDALKDKLGDL (PF-525, SEQ ID NO:23), LSE-MERRRLRKRA (PF-529, SEQ ID NO:24), RRGCTERLRRMARRNAWDLYAEHFY (PF-148, SEQ ID NO:25), SKFKVLRKIIIKEYKGELMLSIQKQR (PF-530, SEQ ID NO:26), FELVDWLETNLGKILKSKSA (PF-522, SEQ ID NO:27), LVLRICTDLFTFIKWTIKQRKS (PF-497, SEQ ID NO:28), VYSFLYVLVIVRKLLSMKKRIERL (PF-499, SEQ ID NO:29), GIVLIGLKLIPLLANVLR (PF-322, SEQ ID NO:30), VMQSLYVKPPLILVTKLAQQN (PF-511, SEQ ID NO:31), SFMPEIQKNTIPTQMK (PF-512, SEQ ID NO:32), LGLTAGVAYAAQPTNQPTNQPTNQPT-NQPTNQPTNQPRW (PF-520, SEQ ID NO:33), CGKLLEQKNFFLKTR (PF-521, SEQ ID NO:34), ASKQASKQASKQASKQASKQASRSLKNHLL (PF-523, SEQ ID NO:35), PDAPRTCYHKPILAALSRIVVTDR (PF-524, SEQ ID NO:36), NYAVVSHT (PF-209, SEQ ID NO:37), ILVLLALQVELDSKFQY (PF-C157, SEQ ID NO:38), YVNYNQSFNSGW (PF-C220, SEQ ID NO:39), and FQKPFTGEEVEDFQDDDEIPTII (PF-437, SEQ ID NO:40) and/or the inverse of these sequences. In certain embodiments the amino acid sequence of the peptide consists of a sequence selected from group consisting of GSVIKKRRKRMSKKKHRKMLRRTRVQRRKLGK (PF-S028, SEQ ID NO:1), NYRLVNAIFSKIFKKKFIKF (PF-C252, SEQ ID NO:2), YIQFHLNQQPRPKVKKIKIFL (PF-531, SEQ ID NO:3), GSVIKKRRKRMAKKKHRKLLKKTRIQRRRAGK (PF-527, SEQ ID NO:4), MRFGSLALVAYDSAIKHSWPRPSS-VRRLRM (PF-672, SEQ ID NO:5), FESKILNASKELD-KEKKVNTALSFNSHQDFAKAYQNGKI (PF-606, SEQ ID NO:6), KGKSLMPLLKQINQWGKLYL (PF-C239, SEQ ID NO:7), WSRVPGHSDTGWKVWHRW (PF-547, SEQ ID NO:8), MGIIAGIIKFIKGLIEKFTGK (PF-006, SEQ ID NO:9), ILNKKPKLPLWKLGKNYFRRFYVLPTFLA (PF-C287, SEQ ID NO:10), RESKLIAMADMIRRRI (PF-545, SEQ ID NO:11), LDPLEPRIAPPGDRSHQGAPACHRD-PLRGRSARDAER (PF-C019, SEQ ID NO:12), MPVSKKRYMLSSAYATALGICYGQVAT-DEKESEITAIPDLLDYLSVEEYLL (PF-C163, SEQ ID NO:13), LSLATFAKIFMTRSNWSLKRFNRL (PF-278, SEQ ID NO:14), MIRIRSPTKKKLNRNSISDWKSNTS-GRFFY (PF-283, SEQ ID NO:15), MKRRRCNWCGKL-FYLEEKSKEAYCCKECRKKAKKVKK (PF-307, SEQ ID NO:16), VLPFPAIPLSRRRACVAAPRPRSRQRAS (PF-168, SEQ ID NO:17), KNKKQTDILEKVKEILDKKKK-TKSVGQKLY (PF-538, SEQ ID NO:18), SLQSQLGPCLH-DQRH (PF-448, SEQ ID NO:19), WKRLWPARILAGHSRRRMRWMVVWRYFAAT (PF-C021, SEQ ID NO:20), KFQGEFT-NIGQSYIVSASHMSTSLNTGK (PF-583, SEQ ID NO:21), TKKIELKRFVDAFVKKSYENYILER-ELKKLIKAINEELPTK (PF-600, SEQ ID NO:22), KFSD-QIDKGQDALKDKLGDL (PF-525, SEQ ID NO:23), LSE-MERRRLRKRA (PF-529, SEQ ID NO:24), RRGCTERLRRMARRNAWDLYAEHFY (PF-148, SEQ ID NO:25), SKFKVLRKIIIKEYKGELMLSIQKQR (PF-530, SEQ ID NO:26), FELVDWLETNLGKILKSKSA (PF-522, SEQ ID NO:27), LVLRICTDLFTFIKWTIKQRKS (PF-497, SEQ ID NO:28), VYSFLYVLVIVRKLLSMKKRIERL (PF-499, SEQ ID NO:29), GIVLIGLKLIPLLANVLR (PF-322, SEQ ID NO:30), VMQSLYVKPPLILVTKLAQQN (PF-511, SEQ ID NO:31), SFMPEIQKNTIPTQMK (PF-512, SEQ ID NO:32), LGLTAGVAYAAQPTNQPTNQPTNQPT-NQPTNQPTNQPRW (PF-520, SEQ ID NO:33), CGKLLEQKNFFLKTR (PF-521, SEQ ID NO:34), ASKQASKQASKQASKQASRSLKNHLL (PF-523, SEQ ID NO:35), PDAPRTCYHKPILAALSRIVVTDR (PF-524, SEQ ID NO:36), NYAVVSHT (PF-209, SEQ ID NO:37), ILVLLALQVELDSKFQY (PF-C157, SEQ ID NO:38), YVNYNQSFNSGW (PF-C220, SEQ ID NO:39), and FQKPFTGEEVEDFQDDDEIPTII (PF-437, SEQ ID NO:40). In certain embodiments the peptide is effective to kill or inhibit the growth or proliferation of a yeast and/or fungus (e.g., *A. niger, C. albicans, T. rubrum, M. furfur*, etc.) where the amino acid sequence of the peptide comprises one or more sequences selected from the group consisting of PF-148, PF-168, PF-448, PF-525, PF-527, PF-529, PF-531, PF-545, PF-672, PF-C019, PF-278, PF-307, PF-672, PF-C021, PF-C157, PF-C220, PF-C252, PF-C287, PF-S028, PF-168, PF-278, PF-283, PF-307, PF-527, PF-531, PF-547, PF-672, PF-C019, PF-C021, PF-C252, and PF-S028. In certain embodiments, the peptide is effective to kill or inhibit the growth and/or proliferation of a bacterium, where the amino acid sequence of the peptide comprises one or more sequences selected from the group consisting of PF-006, PF-530, PF-531, PF-538, PF-C163, PF-C239, PF-C252, PF-C287, PF-006, PF-148, PF-283, PF-307, PF-322, PF-497, PF-499, PF-527, PF-531, PF-545, PF-547, PF-672, PF-S028, PF-522, PF-531, PF-538, PF-600, PF-606, PF-672, PF-C239, PF-C252, PF-006, PF-168, PF-209, PF-527, PF-545, PF-583, PF-606, PF-672, PF-C252, PF-S028, PF-S028, PF-C252, PF-531, PF-527, PF-S028, PF-C163, PF-C239, PF-C252, PF-C287, PF-278, PF-283, PF-527, PF-531, PF-583, PF-606, PF-672, PF-C163, PF-C252, PF-S028, PF-531, PF-547, PF-601, PF-C019, PF-C239, PF-C252, PF-S028, PF-437, PF-448, PF-511, PF-512, PF-520, PF-521, PF-523, PF-524, PF-525, PF-529, PF-600, and PF-606. In various embodiments the bacterium is selected from the group consisting of *A. naeslundii, S. mutans, B. subtilis*, MRSA, *C. difficile, S. epidermidis, S. pneumoniae, E. faecalis, P. gingivalis, E. coli, P. aeruginosa, A. baumannii*, and *F. nucleatum*.

In certain embodiments the peptide is effective to kill or inhibit the growth and/or proliferation of a gram positive bacterium, where the amino acid sequence of the peptide comprises one or more sequences selected from the group consisting of PF-006, PF-148, PF-168, PF-209, PF-278, PF-283, PF-307, PF-322, PF-437, PF-448, PF-497, PF-499, PF-511, PF-512, PF-520, PF-521, PF-522, PF-523, PF-524, PF-525, PF-527, PF-529, PF-531, PF-538, PF-545, PF-547, PF-583, PF-600, PF-601, PF-606, PF-672, PF-C019, PF-C163, PF-C239, PF-C252, PF-C287, PF-S028. In certain embodiments the gram positive bacterium is selected from the group consisting of *A. naeslundii, S. mutans, B. subtilis*, MRSA, *C. difficile, S. epidermidis, S. pneumoniae*, and *E. faecalis*.

In certain embodiments the peptide is effective to kill or inhibit the growth and/or proliferation of gram negative bacterium where the amino acid sequence of the peptide comprises one or more sequences selected from the group consisting of PF-006, PF-527, PF-530, PF-531, PF-538, PF-600, PF-606, PF-C163, PF-C239, PF-C252, PF-C287, and PF-S028. In certain embodiments the of gram negative bacterium is selected from the group consisting of *P. gingivalis*, *E. coli*, *P. aeruginosa*, *A. baumannii*, and *F. nucleatum*.

In various embodiments peptide(s) comprise all "L" amino acids, all "D" amino acids, or a mixture of "L" and "D" amino acids. In various embodiments the peptide(s) are β peptides. The peptide(s) can optionally comprise one or more protecting groups (e.g., an amide on the carboxyl terminus and/or an acetyl on the amino terminus). In certain embodiments the peptide(s) are in a pharmaceutically acceptable carrier (e.g., a carrier suitable for administration via a route selected from the group consisting of topical administration, aerosol administration, administration via inhalation, oral administration, systemic IV application, ocular administration, rectal administration, etc.).

In various embodiments antimicrobial compositions are provided that are effective to kill and/or to inhibit the growth and/or proliferation of a microorganism and/or to inhibit the formation and/or growth and/or maintenance of a biofilm comprising said microorganism. The compositions typically comprise one or more peptides, the amino acid sequences of the peptides comprising or consisting of one or more sequences selected from the group consisting of GSVIKKRRKRMSKKKHRKMLRRTRVQRRKLGK (PF-S028, SEQ ID NO:1), NYRLVNAIFSKIFKKKFIKF (PF-C252, SEQ ID NO:2), YIQFHLNQQPRPKVKKIKIFL (PF-531, SEQ ID NO:3), GSVIKKRRKRMAKKKHRKLLKKTRIQRRRAGK (PF-527, SEQ ID NO:4), MRFGSLALVAYDSAIKHSWPRPSS-VRRLRM (PF-672, SEQ ID NO:5), FESKILNASKELD-KEKKVNTALSFNSHQDFAKAYQNGKI (PF-606, SEQ ID NO:6), KGKSLMPLLKQINQWGKLYL (PF-C239, SEQ ID NO:7), WSRVPGHSDTGWKVWHRW (PF-547, SEQ ID NO:8), MGIIAGIIKFIKGLIEKFTGK (PF-006, SEQ ID NO:9), ILNKKPKLPLWKLGKNYFRRFYVLPTFLA (PF-C287, SEQ ID NO:10), RESKLIAMADMIRRRI (PF-545, SEQ ID NO:11), LDPLEPRIAPPGDRSHQGAPACHRD-PLRGRSARDAER (PF-C019, SEQ ID NO:12), MPVSKKRYMLSSAYATALGICYGQVAT-DEKESEITAIPDLLDYLSVEEYLL (PF-C163, SEQ ID NO:13), LSLATFAKIFMTRSNWSLKRFNRL (PF-278, SEQ ID NO:14), MIRIRSPTKKKLNRNSISDWKSNTS-GRFFY (PF-283, SEQ ID NO:15), MKRRRCNWCGKL-FYLEEKSKEAYCCKECRKKAKKVKK (PF-307, SEQ ID NO:16), VLPFPAIPLSRRRACVAAPRPRSRQRAS (PF-168, SEQ ID NO:17), KNKKQTDILEKVKEILDKKKK-TKSVGQKLY (PF-538, SEQ ID NO:18), SLQSQLGPCLH-DQRH (PF-448, SEQ ID NO:19), WKRLWPARILAGHSRRRMRWMVVWRYFAAT (PF-C021, SEQ ID NO:20), KFQGEFT-NIGQSYIVSASHMSTSLNTGK (PF-583, SEQ ID NO:21), TKKIELKRFVDAFVKKSYENYILER-ELKKLIKAINEELPTK (PF-600, SEQ ID NO:22), KFSD-QIDKGQDALKDKLGDL (PF-525, SEQ ID NO:23), LSE-MERRRLRKRA (PF-529, SEQ ID NO:24), RRGCTERLRRMARRNAWDLYAEHFY (PF-148, SEQ ID NO:25), SKFKVLRKIIIKEYKGELMLSIQKQR (PF-530, SEQ ID NO:26), FELVDWLETNLGKILKSKSA (PF-522, SEQ ID NO:27), LVLRICTDLFTFIKWTIKQRKS (PF-497, SEQ ID NO:28), VYSFLYVLVIVRKLLSMKKRIERL (PF-499, SEQ ID NO:29), GIVLIGLKLIPLLANVLR (PF-322, SEQ ID NO:30), VMQSLYVKPPLILVTKLAQQN (PF-511, SEQ ID NO:31), SFMPEIQKNTIPTQMK (PF-512, SEQ ID NO:32), LGLTAGVAYAAQPTNQPTNQPTNQPT-NQPTNQPTNQPRW (PF-520, SEQ ID NO:33), CGKLLEQKNFFLKTR (PF-521, SEQ ID NO:34), ASKQASKQASKQASKQASKQASRSLKNHLL (PF-523, SEQ ID NO:35), PDAPRTCYHKPILAALSRIVVTDR (PF-524, SEQ ID NO:36), NYAVVSHT (PF-209, SEQ ID NO:37), ILVLLALQVELDSKFQY (PF-C157, SEQ ID NO:38), YVNYNQSFNSGW (PF-C220, SEQ ID NO:39), and FQKPFTGEEVEDFQDDDEIPTII (PF-437, SEQ ID NO:40).

In certain embodiments the composition is effective to kill or inhibit the growth and/or proliferation of a yeast or fungus, and the composition comprises one or more peptides, the amino acid sequences of the peptides comprising one or more sequences or inverse of the sequences independently selected from the group consisting of PF-148, PF-168, PF-448, PF-525, PF-527, PF-529, PF-531, PF-545, PF-672, PF-C019, PF-278, PF-307, PF-672, PF-C021, PF-C157, PF-C220, PF-C252, PF-C287, PF-S028, PF-168, PF-278, PF-283, PF-307, PF-527, PF-531, PF-547, PF-672, PF-C019, PF-C021, PF-C252, and PF-S028.

In certain embodiments the composition is effective to kill or inhibit the growth and/or proliferation of *Aspergillus niger* and the composition comprises one or more peptides, the amino acid sequences of the peptides comprising one or more sequences or inverse of the sequences independently selected from the group consisting of PF-148, PF-168, PF-448, PF-525, PF-527, PF-529, PF-531, PF-545, PF-672, and PF-C019.

In certain embodiments the composition is effective to kill or inhibit the growth and/or proliferation of *Candida albicans* and the composition comprises one or more peptides, the amino acid sequences of the peptides comprising one or more sequences or inverse of the sequences independently selected from the group consisting of PF-278, PF-307, PF-672, PF-C021, PF-C157, PF-C220, PF-C252, and PF-C287.

In certain embodiments the composition is effective to kill or inhibit the growth and/or proliferation of *Malassezia furfur* and the composition comprises a peptide comprising the amino acid sequence of PF-S028.

In certain embodiments the composition is effective to kill or inhibit the growth and/or proliferation of *Trichophyton rubrum* and the composition comprises one or more peptides, the amino acid sequences of the peptides comprising one or more sequences or inverse of the sequences independently selected from the group consisting of PF-168, PF-278, PF-283, PF-307, PF-527, PF-531, PF-547, PF-672, PF-C019, PF-C021, PF-C252, PF-S028.

In certain embodiments the composition is effective to kill or inhibit the growth and/or proliferation of a bacterium and the composition comprises one or more peptides, the amino acid sequences of the peptides comprising one or more sequences or inverse of the sequences independently selected from the group consisting of PF-006, PF-530, PF-531, PF-538, PF-C163, PF-C239, PF-C252, PF-C287, PF-006, PF-148, PF-283, PF-307, PF-322, PF-497, PF-499, PF-527, PF-531, PF-545, PF-547, PF-672, PF-S028, PF-522, PF-531, PF-538, PF-600, PF-606, PF-672, PF-C239, PF-C252, PF-006, PF-168, PF-209, PF-527, PF-545, PF-583, PF-606, PF-672, PF-C252, PF-S028, PF-S028, PF-C252, PF-531, PF-527, PF-S028, PF-C163, PF-C239, PF-C252, PF-C287, PF-278, PF-283, PF-527, PF-531, PF-583, PF-606, PF-672, PF-C163, PF-C252, PF-S028, PF-531, PF-547, PF-601, PF-C019, PF-C239, PF-C252, PF-S028, PF-437, PF-448, PF-511, PF-512, PF-520, PF-521, PF-523, PF-524, PF-525, PF-529, PF-600, and PF-606.

In certain embodiments the composition is effective to kill or inhibit the growth and/or proliferation of a gram positive bacterium and the composition comprises one or more peptides, the amino acid sequences of the peptides comprising one or more sequences or inverse of the sequences independently selected from the group consisting of PF-006, PF-148, PF-168, PF-209, PF-278, PF-283, PF-307, PF-322, PF-437, PF-448, PF-497, PF-499, PF-511, PF-512, PF-520, PF-521, PF-522, PF-523, PF-524, PF-525, PF-527, PF-529, PF-531, PF-538, PF-545, PF-547, PF-583, PF-600, PF-601, PF-606, PF-672, PF-C019, PF-C163, PF-C239, PF-C252, PF-C287, PF-S028.

In certain embodiments the composition is effective to kill or inhibit the growth and/or proliferation of *Actinomyces naeslundii* and the composition comprises one or more peptides, the amino acid sequences of the peptides comprising one or more sequences or inverse of the sequences independently selected from the group consisting of PF-C163, PF-C239, PF-C252, and PF-C287.

In certain embodiments the composition is effective to kill or inhibit the growth and/or proliferation of *Bacillus subtilis* and the composition comprises one or more peptides, the amino acid sequences of the peptides comprising one or more sequences or inverse of the sequences independently selected from the group consisting of PF-006, PF-148, PF-283, PF-307, PF-322, PF-497, PF-499, PF-527, PF-531, PF-545, PF-547, PF-672, and PF-S028.

In certain embodiments the composition is effective to kill or inhibit the growth and/or proliferation of *Clostridium difficile* and the composition comprises one or more peptides, the amino acid sequences of the peptides comprising one or more sequences or inverse of the sequences independently selected from the group consisting of PF-522, PF-531, and PF-538.

In certain embodiments the composition is effective to kill or inhibit the growth and/or proliferation of *Enterococcus faecalis* and the composition comprises one or more peptides comprising the amino acid sequence of PF-672.

In certain embodiments the composition is effective to kill or inhibit the growth and/or proliferation of Methicillin-resistant *Staphylococcus aureus* (MRSA) and the composition comprises one or more peptides, the amino acid sequences of the peptides comprising one or more sequences or inverse of the sequences independently selected from the group consisting of PF-006, PF-168, PF-209, PF-527, PF-545, PF-583, PF-606, PF-672, PF-C252, and PF-S028.

In certain embodiments the composition is effective to kill or inhibit the growth and/or proliferation of *S. epidermidis* and the composition comprises one or more peptides, the amino acid sequences of the peptides comprising one or more sequences or inverse of the sequences independently selected from the group consisting of PF-278, PF-283, PF-527, PF-531, PF-583, PF-606, PF-672, PF-C163, PF-C252, and PF-S028.

In certain embodiments the composition is effective to kill or inhibit the growth and/or proliferation of *Streptococcus mutans* and the composition comprises one or more peptides, the amino acid sequences of the peptides comprising one or more sequences or inverse of the sequences independently selected from the group consisting of PF-531, PF-547, PF-601, PF-C019, PF-C239, PF-C252, and PF-S028.

In certain embodiments the peptide composition is effective to kill or inhibit the growth and/or proliferation of *Streptococcus pneumoniae* and the composition comprises one or more peptides, the amino acid sequences of the peptides comprising one or more sequences or inverse of the sequences independently selected from the group consisting of PF-437, PF-448, PF-511, PF-512, PF-520, PF-521, PF-523, PF-524, PF-525, PF-529, PF-600, and PF-606.

In certain embodiments the composition is effective to kill or inhibit the growth and/or proliferation of a gram negative bacterium and the composition comprises one or more peptides, the amino acid sequences of the peptides comprising one or more sequences or inverse of the sequences independently selected from the group consisting of PF-006, PF-527, PF-530, PF-531, PF-538, PF-600, PF-606, PF-C163, PF-C239, PF-C252, PF-C287, and PF-S028.

In certain embodiments the composition is effective to kill or inhibit the growth and/or proliferation of *Acinetobacter baumannii* and the composition comprises one or more peptides, the amino acid sequences of the peptides comprising one or more sequences or inverse of the sequences independently selected from the group consisting of PF-006, PF-530, PF-531, and PF-538.

In certain embodiments the composition is effective to kill or inhibit the growth and/or proliferation of *Escherichia coli* and the composition comprises one or more peptides, the amino acid sequences of the peptides comprising one or more sequences or inverse of the sequences independently selected from the group consisting of PF-600, and PF-606.

In certain embodiments the composition is effective to kill or inhibit the growth and/or proliferation of *Fusobacterium nucleatum* and the composition comprises one or more peptides, the amino acid sequences of the peptides comprising one or more sequences s or inverse of the sequences elected from the group consisting of PF-C239, and PF-C252.

In certain embodiments the composition is effective to kill or inhibit the growth and/or proliferation of *Pseudomonas aeruginosa* and the composition comprises one or more peptides, the amino acid sequences of the peptides comprising one or more sequences or inverse of the sequences independently selected from the group consisting of PF-S028, PF-C252, PF-531, and PF-527.

In certain embodiments the composition is effective to kill or inhibit the growth and/or proliferation of *Porphyromonas gingivalis* and the composition comprises one or more peptides, the amino acid sequences of the peptides comprising one or more sequences or inverse of the sequences independently selected from the group consisting of PF-S028, PF-C163, PF-C239, PF-C252, and PF-C287.

In various embodiments the one or more peptides comprising the composition comprises all "D" amino acids", all "L" amino acids, or a combination of "D" and "L" amino acids. In various embodiments the one or more peptides comprising the composition is a β peptide. In various embodiments the one or more peptides comprising the composition comprise one or more protecting groups (e.g., an amide on the carboxyl terminus and/or an acetyl on the amino terminus). In certain embodiments the composition comprises a pharmaceutically acceptable carrier (e.g. a carrier suitable for administration via a route selected from the group consisting of topical administration, aerosol administration, administration via inhalation, oral administration, rectal administration, etc.).

Methods are also provided for killing and/or inhibiting the growth and/or proliferation of a microorganism and/or inhibiting the formation, growth or maintenance of a biofilm comprising the microorganism. The methods typically involve contacting the microorganism with one or more antimicrobial peptides as described herein and/or a composition comprising one or more peptides, the amino acid sequences of the peptides comprising one or more sequences or inverse of the sequences independently selected from the group consisting of PF-006, PF-530, PF-531, PF-538, PF-C163, PF-C239, PF-C252, PF-C287, PF-006, PF-148, PF-283, PF-307, PF-322, PF-497, PF-499, PF-527, PF-531, PF-545, PF-547, PF-672, PF-S028, PF-522, PF-531, PF-538, PF-600, PF-606, PF-672, PF-C239, PF-C252, PF-006, PF-168, PF-209, PF-527, PF-545, PF-583, PF-606, PF-672, PF-C252, PF-S028, PF-S028, PF-C252, PF-531, PF-527, PF-S028, PF-C163, PF-C239, PF-C252, PF-C287, PF-278, PF-283, PF-527, PF-531, PF-583, PF-606, PF-672, PF-C163, PF-C252, PF-S028, PF-531, PF-547, PF-601, PF-C019, PF-C239, PF-C252, PF-S028, PF-437, PF-448, PF-511, PF-512, PF-520, PF-521, PF-523, PF-524, PF-525, PF-529, PF-600, and PF-606, e.g., as described herein (see, for example, description supra and AMPs and compositions recited in the claims). In certain embodiments the contacting comprises contacting the microorganism with an amount sufficient to kill or to inhibit the growth or proliferation of said microorganism.

In various embodiments methods of disinfecting a surface are also provided. The methods typically involve contacting the surface with one or more antimicrobial peptides as described herein and/or a composition comprising one or more peptides, the amino acid sequences of the peptides comprising one or more sequences or inverse of the sequences independently selected from the group consisting of PF-006, PF-530, PF-531, PF-538, PF-C163, PF-C239, PF-C252, PF-C287, PF-006, PF-148, PF-283, PF-307, PF-322, PF-497, PF-499, PF-527, PF-531, PF-545, PF-547, PF-672, PF-S028, PF-522, PF-531, PF-538, PF-600, PF-606, PF-672, PF-C239, PF-C252, PF-006, PF-168, PF-209, PF-527, PF-545, PF-583, PF-606, PF-672, PF-C252, PF-S028, PF-S028, PF-C252, PF-531, PF-527, PF-S028, PF-C163, PF-C239, PF-C252, PF-C287, PF-278, PF-283, PF-527, PF-531, PF-583, PF-606, PF-672, PF-C163, PF-C252, PF-S028, PF-531, PF-547, PF-601, PF-C019, PF-C239, PF-C252, PF-S028, PF-437, PF-448, PF-511, PF-512, PF-520, PF-521, PF-523, PF-524, PF-525, PF-529, PF-600, and PF-606, e.g., as described herein (see, for example, description supra and AMPs and compositions recited in the claims). In certain embodiments the surface comprises a surface of a prosthesis and/or medical implant, and/or the surface comprises a surface of a medical device, or a surface of a plant or foodstuff. In certain embodiments the peptide(s) are combined with, or used in conjunction with, a second disinfectant selected from the group consisting of other antimicrobial agent is a disinfectant selected from the group consisting of acetic acid, phosphoric acid, citric acid, lactic, formic, propionic acid, hydrochloric acid, sulfuric acid, nitric acid, sodium hydroxide, potassium hydroxide, sodium carbonate, ammonium hydroxide, ethyl alcohol, isopropyl alcohol, phenol, formaldehyde, glutaraldehyde, hypochlorites, chlorine dioxide, sodium dichloroisocyanurate, chloramine-T, iodine, povidone-iodine, chlorhexidine, hydrogen peroxide, peracetic acid, and benzalkonium chloride.

Also provided is the use one or more antimicrobial peptides as described herein and/or a composition comprising one or more peptides, the amino acid sequences of the peptides comprising one or more sequences or inverse of the sequences independently selected from the group consisting of PF-006, PF-530, PF-531, PF-538, PF-C163, PF-C239, PF-C252, PF-C287, PF-006, PF-148, PF-283, PF-307, PF-322, PF-497, PF-499, PF-527, PF-531, PF-545, PF-547, PF-672, PF-S028, PF-522, PF-531, PF-538, PF-600, PF-606, PF-672, PF-C239, PF-C252, PF-006, PF-168, PF-209, PF-527, PF-545, PF-583, PF-606, PF-672, PF-C252, PF-S028, PF-S028, PF-C252, PF-531, PF-527, PF-S028, PF-C163, PF-C239, PF-C252, PF-C287, PF-278, PF-283, PF-527, PF-531, PF-583, PF-606, PF-672, PF-C163, PF-C252, PF-S028, PF-531, PF-547, PF-601, PF-C019, PF-C239, PF-C252, PF-S028, PF-437, PF-448, PF-511, PF-512, PF-520, PF-521, PF-523, PF-524, PF-525, PF-529, PF-600, and PF-606, e.g., as described herein (see, for example, description supra and AMPs and compositions recited in the claims) in the manufacture of a medicament for killing and/or inhibiting the growth and/or proliferation of a microorganism. In certain embodiments the microorganism is a yeast or fungus and the peptide or composition is a peptide or composition comprising one or more AMPs identified herein as killing a yeast or fungus. In certain embodiments the microorganism is a bacterium and the peptide or composition is a peptide or composition comprising one or more AMPs identified herein as killing a bacterium. In certain embodiments the microorganism is a gram positive bacterium and the peptide or composition is a peptide or composition comprising one or more AMPs identified herein as killing a gram positive bacterium. In certain embodiments the microorganism is a gram negative bacterium and the peptide or composition is a peptide or composition comprising one or more AMPs identified herein as killing a gram negative bacterium.

Definitions

The term "peptide" as used herein refers to a polymer of amino acid residues typically ranging in length from 2 to about 50 or about 60 residues (in certain instances up to about 100 residues). In certain embodiments the peptide ranges in length from about 2, 3, 4, 5, 7, 9, 10, or 11 residues to about 51, 50, 45, 40, 45, 30, 25, 20, or 15 residues. In certain embodiments the peptide ranges in length from about 8, 9, 10, 11, or 12 residues to about 15, 20, 25, 35, 50, or 51 residues. In certain embodiments the amino acid residues comprising the peptide are "L-form" amino acid residues, however, it is recognized that in various embodiments, "D" amino acids can be incorporated into the peptide. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other, "modified linkages" (e.g., where the peptide bond is replaced by an α-ester, a β-ester, a thioamide, phosphonamide, carbomate, hydroxylate, and the like (see, e.g., Spatola (1983) Chem. Biochem. Amino Acids and Proteins 7: 267-357), where the amide is replaced with a saturated amine (see, e.g., Skiles et al., U.S. Pat. No. 4,496,542; and Kaltenbronn et al., (1990) Pp. 969-970 in Proc. 11th American Peptide Symposium, ESCOM Science Publishers, The Netherlands, and the like)).

The term "residue" as used herein refers to natural, synthetic, or modified amino acids. Various amino acid analogues include, but are not limited to 2-aminoadipic acid, 3-aminoadipic acid, beta-alanine (beta-aminopropionic acid), 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, n-ethylglycine, n-ethylasparagine, hydroxylysine, allo-hydroxylysine, 3-hydroxyproline, 4-hydroxyproline, isodesmosine, allo-isoleucine, n-methylglycine, sarcosine, n-methylisoleucine, 6-n-methyllysine, n-methylvaline, norvaline, norleucine, ornithine, and the like. These modified amino acids are illustrative and not intended to be limiting.

"β-peptides" comprise of "β amino acids", which have their amino group bonded to the β carbon rather than the α-carbon as in the 20 standard biological amino acids. The only commonly naturally occurring β amino acid is β-alanine.

Peptoids, or N-substituted glycines, are a specific subclass of peptidomimetics. They are closely related to their natural peptide counterparts, but differ chemically in that their side chains are appended to nitrogen atoms along the molecule's backbone, rather than to the α-carbons (as they are in natural amino acids).

The terms "conventional" and "natural" as applied to peptides herein refer to peptides, constructed only from the naturally-occurring amino acids: Ala, Cys, Asp, Glu, Glu, Phe, Gly, His, Ile, Lys, Leu, Met, Asn, Pro, Gln, Arg, Ser, Thr, Val, Trp, and Tyr. A compound of the invention "corresponds" to a natural peptide if it elicits a biological activity (e.g., antimicrobial activity) related to the biological activity and/or specificity of the naturally occurring peptide. The elicited activity may be the same as, greater than or less than that of the natural peptide. In general, such a peptoid will have an essentially corresponding monomer sequence, where a natural amino acid is replaced by an N-substituted glycine derivative, if the N-substituted glycine derivative resembles the original amino acid in hydrophilicity, hydrophobicity, polarity, etc. The following are illustrative, but non-limiting N-substituted glycine replacements: N-(1-methylprop-1-yl)glycine substituted for isoleucine (Ile), N-(prop-2-yl)glycine for valine (Val), N-benzylglycine for phenylanlaine (Phe), N-(2-hydroxyethyl)glycine for serine (Ser), and the like. In certain embodiments substitutions need not be "exact". Thus for example, in certain embodiments N-(2-hydroxyethyl)glycine may substitute for Ser, Thr, Cys, and/or Met; N-(2-methyl-prop-1-yl)glycine may substitute for Val, Leu, and/or Ile. In certain embodiments N-(2-hydroxyethyl)glycine can be used to substitute for Thr and Ser, despite the structural differences: the side chain in N-(2-hydroxyethyl)glycine is one methylene group longer than that of Ser, and differs from Thr in the site of hydroxy-substitution. In general, one may use an N-hydroxyalkyl-substituted glycine to substitute for any polar amino acid, an N-benzyl- or N-aralkyl-substituted glycine to replace any aromatic amino acid (e.g., Phe, Trp, etc.), an N-alkyl-substituted glycine such as N-butylglycine to replace any nonpolar amino acid (e.g., Leu, Val, Ile, etc.), and an N-(aminoalkyl)glycine derivative to replace any basic polar amino acid (e.g., Lys and Arg).

Where an amino acid sequence is provided herein, L-, D-, or beta amino acid versions of the sequence are also contemplated as well as retro, inversion, and retro-inversion isoforms. In addition, conservative substitutions (e.g., in the binding peptide, and/or antimicrobial peptide, and/or linker peptide) are contemplated. Non-protein backbones, such as PEG, alkane, ethylene bridged, ester backbones, and other backbones are also contemplated. Also fragments ranging in length from about 5, 6, 7, 8, 9, 10, 11, 12, 13, 14, 15, 16, 17, 18, 19, 20, 21, 22, 23, 24, or 25 amino acids up to the full length minus one amino acid of the peptide are contemplated where the fragment retains at least 50%, preferably at least 60% 70% or 80%, more preferably at least 90%, 95%, 98%, 99%, or at least 100% of the activity (e.g., binding specificity and/or avidity, antimicrobial activity, etc.) of the full length peptide are contemplated.

In certain embodiments, conservative substitutions of the amino acids comprising any of the sequences described herein are contemplated. In various embodiments one, two, three, four, or five different residues are substituted. The term "conservative substitution" is used to reflect amino acid substitutions that do not substantially alter the activity (e.g., antimicrobial activity and/or specificity) of the molecule. Typically conservative amino acid substitutions involve substitution one amino acid for another amino acid with similar chemical properties (e.g. charge or hydrophobicity). Certain conservative substitutions include "analog substitutions" where a standard amino acid is replaced by a non-standard (e.g., rare, synthetic, etc) amino acid differing minimally from the parental residue. Amino acid analogs are considered to be derived synthetically from the standard amino acids without sufficient change to the structure of the parent, are isomers, or are metabolite precursors. Examples of such "analog substitutions include but are not limited to 1) Lys-Orn, 2) Leu-Norleucine, 3) Lys-Lys[TFA], 4) Phe-Phe[Gly], and 5) δ-amino butylglycine-ξ-amino hexylglycine, where Phe[gly] refers to phenylglycine (a Phe derivative with a H rather than $CH_3$ component in the R group), and Lys[TFA] refers to a Lys where a negatively charged ion (e.g., TFA) is attached to the amine R group. Other conservative substitutions include "functional substitutions" where the general chemistries of the two residues are similar, and can be sufficient to mimic or partially recover the function of the native peptide. Strong functional substitutions include, but are not limited to 1) Gly/Ala, 2) Arg/Lys, 3) Ser/Tyr/Thr, 4) Leu/Ile/Val, 5) Asp/Glu, 6) Gln/Asn, and 7) Phe/Trp/Tyr, while other functional substitutions include, but are not limited to 8) Gly/Ala/Pro, 9) Tyr/His, 10) Arg/Lys/His, 11) Ser/Thr/Cys, 12) Leu/Ile/Val/Met, and 13) Met/Lys (special case under hydrophobic conditions). Various "broad conservative substations" include substitutions where amino acids replace other amino acids from the same biochemical or biophysical grouping. This is similarity at a basic level and stems from efforts to classify the original 20 natural amino acids. Such substitutions include 1) nonpolar side chains: Gly/Ala/Val/Leu/Ile/Met/Pro/Phe/Trp, and/or 2) uncharged polar side chains Ser/Thr/Asn/Gln/Tyr/Cys. In certain embodiments broad-level substitutions can also occur as paired substitutions. For example, Any hydrophilic neutral pair [Ser, Thr, Gln, Asn, Tyr, Cys]+[Ser, Thr, Gln, Asn, Tyr, Cys] can may be replaced by a charge-neutral charged pair [Arg, Lys, His]+[Asp, Glu]. The following six groups each contain amino acids that, in certain embodiments, are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K), Histidine (H); 5) Isoleucine (I), Leucine (L), Methionine (M), Valine (V); and 6) Phenylalanine (F), Tyrosine (Y), Tryptophan (W). Where amino acid sequences are disclosed herein, amino acid sequences comprising, one or more of the above-identified conservative substitutions are also contemplated.

Antimicrobial peptides described herein also include "compound antimicrobial peptides" or "compound AMP(s)" that are constructs comprising two or more AMPs joined together thus forming a molecule with multiple AMP domains (that are the same or different). The AMPs can be joined directly or through a linker. They can be chemically conjugated or, where joined directly together or through a peptide linker can comprise a fusion protein.

In certain embodiments antimicrobial peptides compromising at least 80%, preferably at least 85% or 90%, and more preferably at least 95% or 98% or 99% sequence identity with any of the sequences described herein are also contemplated. The terms "identical" or percent "identity," refer to two or more sequences that are the same or have a specified percentage of amino acid residues that are the same, when compared and aligned for maximum correspondence, as measured using one of the following sequence comparison algorithms or by visual inspection. With respect to the peptides of this invention sequence identity is determined over the full length of the peptide. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci., USA*, 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

The term "specificity" when used with respect to the antimicrobial activity of a peptide indicates that the peptide preferentially inhibits growth and/or proliferation and/or kills a particular microbial species as compared to other related and/or unrelated microbes.

In certain embodiments the preferential inhibition or killing is at least 10% greater (e.g., $LD_{50}$ is 10% lower), preferably at least 20%, 30%, 40%, or 50%, more preferably at least 2-fold, at least 5-fold, or at least 10-fold greater for the target species.

"Treating" or "treatment" of a condition as used herein may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

The term "consisting essentially of" when used with respect to an antimicrobial peptide (AMP) or AMP motif as described herein, indicates that the peptide or peptides encompassed by the library or variants, analogues, or derivatives thereof possess substantially the same or greater antimicrobial activity and/or specificity as the referenced peptide. In certain embodiments substantially the same or greater antimicrobial activity indicates at least 80%, preferably at least 90%, and more preferably at least 95% of the anti microbial activity of the referenced peptide(s) against a particular bacterial species (e.g., *S. mutans*).

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H$1 by a disulfide bond. The $F(ab)'_2$ may be reduced under mild conditions to break the disulfide linkage in the hinge region thereby converting the $(Fab')_2$ dimer into an Fab' monomer. The Fab' monomer is essentially an Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies, including, but are not limited to, $Fab'_2$, IgG, IgM, IgA, scFv, dAb, nanobodies, unibodies, and diabodies.

In certain embodiments antibodies and fragments of the present invention can be bispecific. Bispecific antibodies or fragments can be of several configurations. For example, bispecific antibodies may resemble single antibodies (or antibody fragments) but have two different antigen binding sites (variable regions). In various embodiments bispecific antibodies can be produced by chemical techniques (Kranz et al. (1981) *Proc. Natl. Acad. Sci., USA,* 78: 5807), by "polydoma" techniques (see, e.g., U.S. Pat. No. 4,474,893), or by recombinant DNA techniques. In certain embodiments bispecific antibodies of the present invention can have binding specificities for at least two different epitopes, at least one of which is an epitope of a microbial organism. The microbial binding antibodies and fragments can also be heteroantibodies. Heteroantibodies are two or more antibodies, or antibody binding fragments (e.g., Fab) linked together, each antibody or fragment having a different specificity.

The term "STAMP" refers to Specifically Targeted Anti-Microbial Peptides. In various embodiments, a STAMP comprises one or more peptide targeting moieties attached to one or more antimicrobial moieties (e.g., antimicrobial peptides (AMPs)). An MH-STAMP is a STAMP bearing two or more targeting domains (i.e., a multi-headed STAMP).

The terms "isolated" "purified" or "biologically pure" refer to material which is substantially or essentially free from components that normally accompany it as found in its native state. In the case of a peptide, an isolated (naturally occurring) peptide is typically substantially free of components with which it is associated in the cell, tissue, or organism. The term isolated also indicates that the peptide is not present in a phage display, yeast display, or other peptide library.

In various embodiments the amino acid abbreviations shown in Table 1 are used herein.

TABLE 1

Various amino acid abbreviations.

| Name | Abbreviation | |
|---|---|---|
| | 3 Letter | 1 Letter |
| Alanine | Ala | A |
| βAlanine ($NH_2$—$CH_2$—$CH_2$—COOH) | βAla | |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |

TABLE 1-continued

Various amino acid abbreviations.

| Name | 3 Letter | 1 Letter |
|---|---|---|
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| episilon-aminocaproic acid ($NH^2$—$(CH_2)_5$—COOH) | Ahx | J |
| 4-aminobutanoic acid ($NH_2$—$(CH_2)_3$—COOH) | gAbu | |
| tetrahydroisoquinoline-3-carboxylic acid | | O |
| Lys(N(epsilon)-trifluoroacetyl) | | K[TFA] |
| α-aminoisobutyric acid | Aib | B |

BRIEF DESCRIPTION OF THE DRAWINGS

FIG. 1. Killing kinetics of PF-S028 L and D versions against *M. furfur* were determined using standard time-kill methods previously detailed (Eckert et al. (2006) *Antimicrob Agents Chemother.*, 50: 1480-1488). Briefly, a log phase culture of *M. furfur* ATCC 14521 was diluted to $10^6$ cells/ml in ATCC medium 1072. To the reaction tubes 5 µM of either PF-S028 L or PF-S028 D were added. A reaction tube to which 4 µl of 50% methanol served as the negative control. Reaction tubes were stored at 30° C. and at indicated intervals an aliquot was removed from the reaction tube and placed in a recovery tube where peptide was removed by dilution. An aliquot from the recovery tube was plated on ATCC medium 1072 agar plates and incubated at 30° C. until visible colonies formed. Colony forming units were calculated for the negative control (no peptide), PF-S028 L, and PF-S028 D treated cultures. After 15 min of treatment, PF-S028 D killed over 99% of the *M. furfur*. PF-S028 L killed 39%.

DETAILED DESCRIPTION

In various embodiments novel peptides having antimicrobial activity against certain bacteria, fungi, and/or yeasts are provided. When exploited for their antimicrobial activity, the novel antimicrobial peptides described herein (see, e.g., Table 3) can be used to inhibit the growth and/or proliferation of a microbial species and/or the growth and/formation and/or maintenance of a biofilm comprising the microbial species. In various embodiments the peptides can be formulated individually, in combination with each other, in combination with other antimicrobial peptides, and/or in combination with various antibacterial agents to provide antimicrobial reagents and/or pharmaceuticals.

Accordingly, in certain embodiments this invention provides peptides having antimicrobial activity, compositions comprising the peptides, methods of using the peptides (or compositions thereof) to inhibit the growth of or kill a wide variety of microbial targets and methods of using the peptides (or compositions thereof) to treat or prevent microbial infections and diseases related thereto in both plants and animals.

The various peptides described herein exhibit antimicrobial activity, being biostatic or biocidal against a certain microbial targets, including but not limited to, Gram-negative bacteria such as *Acinetobacter baumannii*, *Escherichia coli*, *Fusobacterium nucleatum*, *Pseudomonas aeruginosa*, *Porphyromonas gingivalis*; Gram-positive bacteria such as *Actinomyces naeslundii*, *Bacillus subtilis*, *Clostridium difficile*, *Enterococcus faecalis*, *Staphylococcus aureus* (and MRSA), *S. epidermidis*, *Streptococcus mutans*, *Streptococcus pneumoniae*; and yeast or fungi such as *Aspergillus niger*, *Candida albicans*, *Malassezia furfur*, and *Trichophyton rubrum* (see, e.g., Table 2). Significantly, various peptides described herein are biostatic or biocidal against clinically relevant pathogens exhibiting multi-drug resistance such as, for example, methicillin-resistant *Staphylococcus aureus* ("MRSA").

TABLE 2

Illustrative target microorganisms and associated pathology.

| | |
|---|---|
| *Acinetobacter baumannii* (*A. baumannii*) | Pathogenic gram-negative bacillus that is naturally sensitive to relatively few antibiotics. |
| *Actinomyces naeslundii* (*A. naeslundii*) | Gram positive rod shaped bacteria that occupy the oral cavity and are implicated in periodontal disease and root caries. |
| *Aspergillus niger* (*A. niger*) | A fungal infection that often causes a black mould to appear on some fruit and vegetables but may also infect humans through inhalation of fungal spores. |
| *Bacillus subtilis* (*B. subtilis*) | Gram-positive, catalase-positive bacterium. |
| *Candida albicans* (*C. albicans*) | Causal agent of opportunistic oral and genital fungal infections in humans. |
| *Clostridium difficile* (*C. difficile*) | A gram-positive, anaerobic, spore-forming *bacillus* that is responsible for the development of antibiotic-associated diarrhea and colitis. |
| *Corynebacterium jeikium* (*C. jeikium*) | Gram-positive, normal skin flora associated with malodor. Opportunistic pathogen. |
| *Escherichia coli* (*E. coli*) | Gram negative rod-shaped bacterium commonly found in the lower intestine of warm-blooded organisms. Certain strains cause serious food poisoning in humans. |
| *Enterococcus faecalis* (*E. faecalis*) | Gram-positive commensal bacterium and opportunistic pathogen. |
| *Fusobacterium nucleatum* (*E. nucleatum*) | Gram negative schizomycetes bacterium often seen in necrotic tissue and implicated, but not conclusively, with other organisms in the causation and perpetuation of periodontal disease. |
| *Malassezia furfur* (*M. furfur*) | yeast - cutaneous pathogen |
| Methicillin-resistant *Staphylococcus aureus* (MRSA) | Any strain of *Staphylococcus aureus* bacteria (gram positive) that is resistant to a one or more members of a large group of antibiotics called the beta-lactams. Responsible for skin and systemic infections. |
| *Pseudomonas aeruginosa* *P. aeruginosa* | Gram-negative rod, common opportunistic pathogen. Responsible for lung, ear, and skin infections. Second most prevalent source of burn wound infections. |
| *Porphyromonas gingivalis* (*P. gingivalis*) | Belongs to the genus *Bacteroides* and is a non-motile, gram-negative, rod-shaped, anaerobic pathogenic bacterium (periodontal disease) |
| *S. epidermidis* (*S. epidermidis*) | Gram-positive, coagulase-negative cocci. Nosocomial pathogen associated with infection (biofilm) of implanted medical devices. |
| *Streptococcus mutans* (*S. mutans*) | Gram-positive, facultatively anaerobic bacterium commonly found in the human oral cavity and is the primary contributor to tooth decay |
| *Streptococcus pneumoniae* (*S. pneumoniae*) | Gram-positive, alpha-hemolytic, bile soluble aerotolerant anaerobe. Causal agent for streptococcal pneumonia. |
| *Trichophyton rubrum* (*T. rubrum*) | Most common cause of athlete's foot, jock itch and ringworm. |

In certain embodiments, the antimicrobial peptide is attached to an opsinon or lysosome uptake or internalization signal to facilitate cellular uptake and killing of intracellular microorganisms.

I. Antimicrobial Peptides.

In certain embodiments the antimicrobial peptides include peptides comprising or consisting of one or more of the amino acid sequences shown in Table 3 (SEQ ID NOs:1-40). In various embodiments the peptides include peptides comprising or consisting of the retro, inverso, retro-inverso, and/or beta form of one or more of the amino acid sequences shown in Table 3 (SEQ ID NOs:1-40). Also contemplated are circular permutations of these sequences as well as peptides comprising or consisting of the retro, inverso, retro-inverso, and/or or beta form of such circular permutations.

It will also be recognized, that in certain embodiments, any peptide or compound AMP described herein can be circularized.

In various embodiments the peptides can optionally bear one or more protecting groups, e.g., and the amino and/or carboxyl termini, and/or on side chains.

Also contemplated are peptides comprising one, two, three four, or five conservative substitutions of these amino acid sequences.

TABLE 3

Illustrative antimicrobial peptide sequences, target organisms and the MIC (lowest concentration of an antibiotic which will inhibit the (in vitro) growth) of the listed target organism(s).

| Name | Amino Acid Sequence | Organisms | MIC (μM) | SEQ ID No. |
|---|---|---|---|---|
| PF-S028 | GSVIKKRRKRMSKKKHRKMLRRTR VQRRKLGK | P. aeruginosa<br>P. gingivalis<br>T. rubrum<br>M. furfur<br>B. subtilis<br>C. jeikeium<br>MRSA<br>S. epidermidis<br>S. mutans | 50<br>25<br>50<br>2.5<br>12.5<br>6.25<br>50<br>25<br>50 | 1 |
| PF-C252 | NYRLVNAIFSKIFKKKFIKF | P. aeruginosa<br>P. gingivalis<br>C. albicans<br>T. rubrum<br>A. naeslundii<br>F. nucleatum<br>MRSA<br>S. epidermidis<br>S. mutans | 50<br>25<br>25<br>50<br>25<br>25<br>50<br>25<br>12.5 | 2 |
| PF-531 | YIQFHLNQQPRPKVKKIKIFL | A. baumannii<br>P. aeruginosa<br>T. rubrum<br>A. niger<br>B. subtilis<br>C. difficile<br>C. jeikeium<br>S. epidermidis<br>S. mutans | 25<br>50<br>50<br>25<br>25<br>12.5<br>6.25<br>50<br>12.5 | 3 |
| PF-527 | GSVIKKRRKRMAKKKHRKLLKKTRI QRRRAGK | P. aeruginosa<br>T. rubrum<br>A. niger<br>B. subtilis<br>C. jeikeium<br>MRSA<br>S. epidermidis | 50<br>25<br>50<br>12.5<br>6.25<br>50<br>25 | 4 |
| PF-672 | MRFGSLALVAYDSAIKHSWPRPSSV RRLRM | C. albicans<br>T. rubrum<br>A. niger<br>B. subtilis<br>E. faecalis<br>MRSA<br>S. epidermidis | 1.56<br>0.78<br>3<br>0.78<br>3.13<br>1.56<br>0.39 | 5 |
| PF-606 | FESKILNASKELDKEKKVNTALSFNS HQDFAKAYQNGKI | E. coli<br>MRSA<br>S. epidermidis<br>S. mutans<br>S. pneumoniae | 50<br>50<br>50<br>50<br>50 | 6 |
| PF-C239 | KGKSLMPLLKQINQWGKLYL | P. gingivalis<br>A. naeslundii<br>F. nucleatum<br>S. mutans | 50<br>25<br>50<br>50 | 7 |

TABLE 3-continued

Illustrative antimicrobial peptide sequences, target organisms and the MIC (lowest concentration of an antibiotic which will inhibit the (in vitro) growth) of the listed target organism(s).

| Name | Amino Acid Sequence | Organisms | MIC (μM) | SEQ ID No. |
|---|---|---|---|---|
| PF-547 | WSRVPGHSDTGWKVWHRW | T. rubrum<br>B. subtilis<br>S. mutans | 25<br>25<br>12.5 | 8 |
| PF-006 | MGIIAGIIKFIKGLIEKFTGK | A. baumannii<br>B. subtilis<br>MRSA | 50<br>25<br>50 | 9 |
| PF-C287 | ILNKKPKLPLWKLGKNYFRRFYVLPTFLA | P. gingivalis<br>C. albicans<br>A. naeslundii | 50<br>50<br>25 | 10 |
| PF-545 | RESKLIAMADMIRRRI | A. niger<br>B. subtilis<br>MRSA | 50<br>25<br>50 | 11 |
| PF-C019 | LDPLEPRIAPPGDRSHQGAPACHRDPLRGRSARDAER | T. rubrum<br>A. niger<br>S. mutans | 50<br>50<br>25 | 12 |
| PF-C163 | MPVSKKRYMLSSAYATALGICYGQVATDEKESEITAIPDLLDYLSVEEYLL | P. gingivalis<br>A. naeslundii<br>S. epidermidis | 50<br>50<br>50 | 13 |
| PF-278 | LSLATFAKIFMTRSNWSLKRFNRL | C. albicans<br>T. rubrum<br>S. epidermidis | 50<br>50<br>50 | 14 |
| PF-283 | MIRIRSPTKKKLNRNSISDWKSNTSGRFFY | T. rubrum<br>B. subtilis<br>S. epidermidis | 50<br>50<br>50 | 15 |
| PF-307 | MKRRRCNWCGKLFYLEEKSKEAYCCKECRKKAKKVKK | C. albicans<br>T. rubrum<br>B. subtilis | 50<br>50<br>50 | 16 |
| PF-168 | VLPFPAIPLSRRRACVAAPRPRSRQRAS | T. rubrum<br>A. niger<br>MRSA | 50<br>50<br>50 | 17 |
| PF-538 | KNKKQTDILEKVKEILDKKKKTKSVGQKLY | A. baumannii<br>C. difficile | 25<br>25 | 18 |
| PF-448 | SLQSQLGPCLHDQRH | A. niger<br>S. pneumoniae | 25<br>50 | 19 |
| PF-C021 | WKRLWPARILAGHSRRRMRWMVVWRYFAAT | C. albicans<br>T. rubrum | 50<br>50 | 20 |
| PF-583 | KFQGEFTNIGQSYIVSASHMSTSLNTGK | MRSA<br>S. epidermidis | 50<br>50 | 21 |
| PF-600 | TKKIELKRFVDAFVKKSYENYILERELKKLIKAINEELPTK | E. coli<br>S. pneumoniae | 50<br>50 | 22 |
| PF-525 | KFSDQIDKGQDALKDKLGDL | A. niger<br>S. pneumoniae | 50<br>50 | 23 |
| PF-529 | LSEMERRRLRKRA | A. niger<br>S. pneumoniae | 50<br>50 | 24 |
| PF-148 | RRGCTERLRRMARRNAWDLYAEHFY | A. niger<br>B. subtilis | 50<br>50 | 25 |
| PF-530 | SKFKVLRKIIIKEYKGELMLSIQKQR | A. baumannii | 25 | 26 |
| PF-522 | FELVDWLETNLGKILKSKSA | C. difficile | 25 | 27 |
| PF-497 | LVLRICTDLFTFIKWTIKQRKS | B. subtilis | 50 | 28 |
| PF-499 | VYSFLYVLVIVRKLLSMKKRIERL | B. subtilis | 50 | 29 |

TABLE 3-continued

Illustrative antimicrobial peptide sequences, target organisms and the MIC (lowest concentration of an antibiotic which will inhibit the (in vitro) growth) of the listed target organism(s).

| Name | Amino Acid Sequence | Organisms | MIC (µM) | SEQ ID No. |
|---|---|---|---|---|
| PF-322 | GIVLIGLKLIPLLANVLR | B. subtilis | 50 | 30 |
| PF-511 | VMQSLYVKPPLILVTKLAQQN | S. pneumoniae | 50 | 31 |
| PF-512 | SFMPEIQKNTIPTQMK | S. pneumoniae | 50 | 32 |
| PF-520 | LGLTAGVAYAAQPTNQPTNQPTNQPTNQPTNQPTNQPRW | S. pneumoniae | 50 | 33 |
| PF-521 | CGKLLEQKNFFLKTR | S. pneumoniae | 50 | 34 |
| PF-523 | ASKQASKQASKQASKQASKQASRSLKNHLL | S. pneumoniae | 50 | 35 |
| PF-524 | PDAPRTCYHKPILAALSRIVVTDR | S. pneumoniae | 50 | 36 |
| PF-209 | NYAVVSHT | MRSA | 50 | 37 |
| PF-C157 | ILVLLALQVELDSKFQY | C. albicans | 50 | 38 |
| PF-C220 | YVNYNQSFNSGW | C. albicans | 50 | 39 |
| PF-437 | FQKPFTGEEVEDFQDDDEIPTII | S. pneumoniae | 50 | 40 |

In certain embodiments, the amino acid sequence of the antimicrobial peptides comprises or consists of a single amino acid sequence, e.g., as listed above. In certain embodiments the amino acid sequence of the antimicrobial peptides comprises two copies, three copies, four copies, five copies six copies or more of one or more of the amino acid sequences listed above. Thus, compound antimicrobial constructs are contemplated where the construct comprises multiple domains each having antimicrobial activity. The AMP domains comprising such a construct can be the same or different. In certain embodiments the construct comprises at least 2, at least 3, at least 4, at least 5, at least 6, at least 7, or at least 8 different AMP domains each domain comprising a different AMP sequence.

Various AMP domains comprising such a construct can be joined directly to each other or two or more of such domains can be attached to each other via a linker. An illustrative, but non-limiting, list of suitable linkers is provided in Table 4.

TABLE 4

Illustrative peptide and non-peptide linkers for joining AMP domains and/or for joining AMPs and/or compound AMPs to one or more targeting or other moieties.

| Linker | SEQ ID NO: |
|---|---|
| AAA | |
| GGG | |
| GGGG | 41 |
| GGGGG | 42 |
| SGG | |
| GGSGGS | 43 |
| SAT | |
| PYP | |
| PSPSP | 44 |
| ASA | |
| ASASA | 45 |
| PSPSP | 46 |
| KKKK | 47 |
| RRRR | 48 |

TABLE 4-continued

Illustrative peptide and non-peptide linkers for joining AMP domains and/or for joining AMPs and/or compound AMPs to one or more targeting or other moieties.

| Linker | SEQ ID NO: |
|---|---|
| Gly$_4$Ser | 49 |
| (Gly$_4$Ser)$_2$ | 50 |
| (Gly$_4$Ser)$_3$ | 51 |
| (Gly$_4$Ser)$_4$ | 52 |
| (Gly$_4$Ser)$_5$ | 53 |
| (Gly$_4$Ser)$_6$ | 54 |
| 2-nitrobenzene or O-nitrobenzyl | |
| Nitropyridyl disulfide | |
| Dioleoylphosphatidylethanolamine (DOPE) | |
| S-acetylmercaptosuccinic acid | |
| 1,4,7,10-tetraazacyclododecane-1,4,7,10-tetracetic acid (DOTA) | |
| β-glucuronide and β-glucuronide variants | |
| Poly(alkylacrylic acid) | |
| Benzene-based linkers (for example: 2,5-Bis(hexyloxy)-1,4-bis[2,5-bis(hexyloxy)-4-formyl-phenylenevinylene]benzene) and like. | |
| Disulfide linkages | |
| Poly(amidoamine) or like dendrimers linking multiple target and killing peptides in one molecule | |
| Carbon nanotubes | |
| Hydrazone and hydrazone variant linkers | |
| PEG of any chain length | |
| Succinate, formate, acetate butyrate, other like organic acids | |
| Aldols, alcohols, or enols | |
| Peroxides | |
| Alkane or alkene groups of any chain length | |
| One or more porphyrin or dye molecules containing free amide and carboxylic acid groups | |
| One or more DNA or RNA nucleotides, including polyamine and polycarboxyl-containing variants | |
| Inulin, sucrose, glucose, or other single, di or polysaccharides | |
| Linoleic acid or other polyunsaturated fatty acids | |
| Variants of any of the above linkers containing halogen or thiol groups | |

(all amino-acid-based linkers could be L, D, β, or other forms)

Thus, in certain embodiments, two or more AMP domains comprising a compound AMP construct are chemically conjugated together.

In certain embodiments the two or more AMP domains comprising the AMP construct are joined by a peptide linker. Where all the AMP domains are attached directly to each other or are joined by peptide linkers, the entire construct can be provided as a single-chain peptide (fusion protein).

In various embodiments, the antimicrobial peptides described herein comprise one or more of the amino acid sequences shown in Table 3 (and/or the retro, inverso, retro-inverso, etc. forms of such sequences). In certain embodiments the peptides range in length up to about 100 amino acids in length, preferably up to about 80, about 70, about 60, or about 51 amino acids in length. In certain embodiments the peptides range in length from about 8 amino acids up to about 100 amino acids 80 amino acids, 60 amino acids or about 51 amino acids in length. In certain embodiments the peptides range in length from about 8 up to about 50, 40, 30, 20, 15, 15, 13, or 12 amino acids in length.

As shown in Tables 3 and 5, the various amino acid sequences described herein are effective against particular microorganisms. The range of activity of the peptides or compositions comprising such peptides can be increased by including amino acid sequences effective against different microorganisms either as separate components and/or as multiple domains within a single construct.

TABLE 5

Illustrative target microorganisms and peptides effective against that target microorganism.

| Organism | Peptide | Organism | Peptide |
|---|---|---|---|
| Gram Positive Bacteria: | | | |
| A. naeslundii | PF-C163 | C. difficile | PF-522 |
|  | PF-C239 |  | PF-531 |
|  | PF-C252 |  | PF-538 |
|  | PF-C287 |  |  |
| S. mutans | PF-531 | S. epidermidis | PF-278 |
|  | PF-547 |  | PF-283 |
|  | PF-601 |  | PF-527 |
|  | PF-C019 |  | PF-531 |
|  | PF-C239 |  | PF-583 |
|  | PF-C252 |  | PF-606 |
|  | PF-S028 |  | PF-672 |
|  |  |  | PF-C163 |
|  |  |  | PF-C252 |
|  |  |  | PF-S028 |
| B. subtilis | PF-006 | S. pneumoniae | PF-437 |
|  | PF-148 |  | PF-448 |
|  | PF-283 |  | PF-511 |
|  | PF-307 |  | PF-512 |
|  | PF-322 |  | PF-520 |
|  | PF-497 |  | PF-521 |
|  | PF-499 |  | PF-523 |
|  | PF-527 |  | PF-524 |
|  | PF-531 |  | PF-525 |
|  | PF-545 |  | PF-529 |
|  | PF-547 |  | PF-600 |
|  | PF-672 |  | PF-606 |
|  | PF-S028 |  |  |
| MRSA | PF-006 | E. faecalis | PF-672 |
|  | PF-168 |  |  |
|  | PF-209 |  |  |
|  | PF-527 |  |  |
|  | PF-545 |  |  |
|  | PF-583 |  |  |
|  | PF-606 |  |  |
|  | PF-672 |  |  |
|  | PF-C252 |  |  |
|  | PF-S028 |  |  |

TABLE 5-continued

Illustrative target microorganisms and peptides effective against that target microorganism.

| Organism | Peptide | Organism | Peptide |
|---|---|---|---|
| C. jeikium | PF-531 | | |
|  | PF-S028 | | |
|  | PF-527 | | |
| Gram Negative Bacteria: | | | |
| P. gingivalis | PF-S028 | A. baumannii | PF-006 |
|  | PF-C163 |  | PF-530 |
|  | PF-C239 |  | PF-531 |
|  | PF-C252 |  | PF-538 |
|  | PF-C287 |  |  |
| E. coli | PF-600 | F. nucleatum | PF-C239 |
|  | PF-606 |  | PF-C252 |
| P. aeruginosa | PF-S028 |  |  |
|  | PF-C252 |  |  |
|  | PF-531 |  |  |
|  | PF-527 |  |  |
| Yeast/Fungi: | | | |
| A. niger | PF-148 | T. rubrum | PF-168 |
|  | PF-168 |  | PF-278 |
|  | PF-448 |  | PF-283 |
|  | PF-525 |  | PF-307 |
|  | PF-527 |  | PF-527 |
|  | PF-529 |  | PF-531 |
|  | PF-531 |  | PF-547 |
|  | PF-545 |  | PF-672 |
|  | PF-672 |  | PF-C019 |
|  | PF-C019 |  | PF-C021 |
|  |  |  | PF-C252 |
|  |  |  | PF-S028 |
| C. albicans | PF-278 | M. furfur | PF-S028 |
|  | PF-307 |  |  |
|  | PF-672 |  |  |
|  | PF-C021 |  |  |
|  | PF-C157 |  |  |
|  | PF-C220 |  |  |
|  | PF-C252 |  |  |
|  | PF-C287 |  |  |

Conversely, the activity against a particular microorganism or group of microorganisms can be increased by increasing the number of peptides or peptide domains with activity against that microorganism or group of microorganisms.

Thus, for example, in certain embodiments, a peptide or composition effective to kill or inhibit the growth or proliferation of a yeast or fungus can comprise one or more peptides and/or one or more peptide domains having sequences selected from the group consisting of PF-148, PF-168, PF-448, PF-525, PF-527, PF-529, PF-531, PF-545, PF-672, PF-C019, PF-278, PF-307, PF-672, PF-C021, PF-C157, PF-C220, PF-C252, PF-C287, PF-S028, PF-168, PF-278, PF-283, PF-307, PF-527, PF-531, PF-547, PF-672, PF-C019, PF-C021, PF-C252, and PF-S028. A peptide or composition effective to kill or inhibit the growth or proliferation of *Aspergillus niger* can comprise one or more peptides and/or one or more peptide domains having sequences selected from the group consisting of PF-148, PF-168, PF-448, PF-525, PF-527, PF-529, PF-531, PF-545, PF-672, and PF-C019. A peptide or composition effective to kill or inhibit the growth or proliferation of *Candida albicans* can comprise one or more peptides and/or one or more peptide domains having sequences selected from the group consisting of PF-278, PF-307, PF-672, PF-C021, PF-C157, PF-C220, PF-C252, and PF-C287. A peptide or composition effective to kill or inhibit the growth or proliferation of *Malassezia furfur* can comprise a peptides and/or a peptide domains having sequence of PF-S028. A peptide or composition effective to kill or inhibit the growth or proliferation of *Trichophyton*

*rubrum* can comprise one or more peptides and/or one or more peptide domains having sequences selected from the group consisting of PF-168, PF-278, PF-283, PF-307, PF-527, PF-531, PF-547, PF-672, PF-C019, PF-C021, PF-C252, PF-S028.

In certain embodiments a peptide or composition effective to kill or inhibit the growth or proliferation of a bacterium can comprise one or more peptides and/or one or more peptide domains having sequences selected from the group consisting of PF-006, PF-530, PF-531, PF-538, PF-C163, PF-C239, PF-C252, PF-C287, PF-006, PF-148, PF-283, PF-307, PF-322, PF-497, PF-499, PF-527, PF-531, PF-545, PF-547, PF-672, PF-S028, PF-522, PF-531, PF-538, PF-600, PF-606, PF-672, PF-C239, PF-C252, PF-006, PF-168, PF-209, PF-527, PF-545, PF-583, PF-606, PF-672, PF-C252, PF-S028, PF-S028, PF-C252, PF-531, PF-527, PF-S028, PF-C163, PF-C239, PF-C252, PF-C287, PF-278, PF-283, PF-527, PF-531, PF-583, PF-606, PF-672, PF-C163, PF-C252, PF-S028, PF-531, PF-547, PF-601, PF-C019, PF-C239, PF-C252, PF-S028, PF-437, PF-448, PF-511, PF-512, PF-520, PF-521, PF-523, PF-524, PF-525, PF-529, PF-600, and PF-606.

In certain embodiments a peptide or composition effective to kill or inhibit the growth or proliferation of a gram positive bacterium can comprise one or more peptides and/or one or more peptide domains having sequences selected from the group consisting of PF-006, PF-148, PF-168, PF-209, PF-278, PF-283, PF-307, PF-322, PF-437, PF-448, PF-497, PF-499, PF-511, PF-512, PF-520, PF-521, PF-522, PF-523, PF-524, PF-525, PF-527, PF-529, PF-531, PF-538, PF-545, PF-547, PF-583, PF-600, PF-601, PF-606, PF-672, PF-C019, PF-C163, PF-C239, PF-C252, PF-C287, PF-S028. A peptide or composition effective to kill or inhibit the growth or proliferation of *Actinomyces naeslundii* can comprise one or more peptides and/or one or more peptide domains having sequences selected from the group consisting of PF-C163, PF-C239, PF-C252, and PF-C287. A peptide or composition effective to kill or inhibit the growth or proliferation *Bacillus subtilis* can comprise one or more peptides and/or one or more peptide domains having sequences selected from the group consisting of PF-006, PF-148, PF-283, PF-307, PF-322, PF-497, PF-499, PF-527, PF-531, PF-545, PF-547, PF-672, and PF-S028. A peptide or composition effective to kill or inhibit the growth or proliferation of *Clostridium difficile* can comprise one or more peptides and/or one or more peptide domains having sequences selected from the group consisting of PF-522, PF-531, and PF-538. A peptide or composition effective to kill or inhibit the growth or proliferation of *Enterococcus faecalis* can comprise a peptide and/or one or more peptide domain having the amino acid sequence of PF-672. A peptide or composition effective to kill or inhibit the growth or proliferation of Methicillin-resistant *Staphylococcus aureus* (MRSA) can comprise one or more peptides and/or one or more peptide domains having sequences selected from the group consisting of PF-006, PF-168, PF-209, PF-527, PF-545, PF-583, PF-606, PF-672, PF-C252, and PF-S028. A peptide or composition effective to kill or inhibit the growth or proliferation of *S. epidermidis* can comprise one or more peptides and/or one or more peptide domains having sequences selected from the group consisting of PF-278, PF-283, PF-527, PF-531, PF-583, PF-606, PF-672, PF-C163, PF-C252, and PF-S028. A peptide or composition effective to kill or inhibit the growth or proliferation of *Streptococcus* can comprise one or more peptides and/or one or more peptide domains having sequences selected from the group consisting of PF-531, PF-547, PF-601, PF-C019, PF-C239, PF-C252, and PF-S028. A peptide or composition effective to kill or inhibit the growth or proliferation of *Streptococcus pneumoniae* can comprise one or more peptides and/or one or more peptide domains having sequences selected from the group consisting of PF-437, PF-448, PF-511, PF-512, PF-520, PF-521, PF-523, PF-524, PF-525, PF-529, PF-600, and PF-606.

In certain embodiments a peptide or composition effective to kill or inhibit the growth or proliferation of effective to kill or inhibit the growth or proliferation of a gram negative bacterium can comprise one or more peptides and/or one or more peptide domains having sequences selected from the group consisting of PF-006, PF-527, PF-530, PF-531, PF-538, PF-600, PF-606, PF-C163, PF-C239, PF-C252, PF-C287, and PF-S028. A peptide or composition effective to kill or inhibit the growth or proliferation of *Acinetobacter baumannii* can comprise one or more peptides and/or one or more peptide domains having sequences selected from the group consisting of PF-006, PF-530, PF-531, and PF-538. A peptide or composition effective to kill or inhibit the growth or proliferation of *Escherichia coli* can comprise one or more peptides and/or one or more peptide domains having sequences selected from the group consisting of PF-600, and PF-606. A peptide or composition effective to kill or inhibit the growth or proliferation of *Fusobacterium nucleatum* can comprise one or more peptides and/or one or more peptide domains having sequences selected from the group consisting of PF-C239, and PF-C252. A peptide or composition effective to kill or inhibit the growth or proliferation of *Pseudomonas aeruginosa* can comprise one or more peptides and/or one or more peptide domains having sequences selected from the group consisting of PF-S028, PF-C252, PF-531, and PF-527. A peptide or composition effective to kill or inhibit the growth or proliferation of *Porphyromonas gingivalis* can comprise one or more peptides and/or one or more peptide domains having sequences selected from the group consisting of PF-S028, PF-C163, PF-C239, PF-C252, and PF-C287.

A peptide or composition effective to kill or inhibit the growth or proliferation of *Corynebacterium jeikium* can comprise one or more peptides and/or one or more peptide domains having sequences selected from the group consisting of PF-531, PF-S028, PF-527.

II. Chimeric Constructs.

In various embodiments this invention provides chimeric moieties comprising antimicrobial peptides attached to targeting moieties, to detectable labels, and/or to opsonins, lysosomes, or other internalization signals.

Targeted Antimicrobial Peptides.

In certain embodiments the antimicrobial peptides (e.g., peptides comprising one or more amino acid sequences found in Table 3) can be attached (directly or through a linker) to one or more targeting moieties to specifically or preferentially deliver the AMP construct to a target microorganism, to a particular cell or tissue, and the like. In various embodiments the targeting moieties preferentially and/or specifically bind to a microorganism (e.g., a bacterium, a fungus, a yeast, etc.).

Targeting Peptides.

In certain embodiments the targeting moieties include, but are not limited to peptides that preferentially bind particular microorganisms (e.g., bacteria, fungi, yeasts, protozoa, algae, viruses, etc.) or groups of such microorganisms, antibodies that bind particular microorganisms or groups of microorganisms, receptor ligands that bind particular microorganisms or groups of microorganisms, porphyrins (e.g., metalloporphyrins), lectins that bind particular microorganisms or groups of microorganisms, and the like. As indicated it will be appreciated that references to microorganisms or groups of microorganism can include bacteria or groups of bacteria, viruses or groups of viruses, yeasts or groups of yeasts, protozoa or groups of protozoa, viruses or groups of viruses, and the like.

Suitable targeting peptides are disclosed, for example in US Patent Publication No: 2008-0170991 (WO/2008/030988) and include for example, C16 (TFFRLFNRS-FTQALGK, SEQ ID NO:55), M8 (TFFRLFNR, SEQ ID NO:56), 1903 (NIFEYFLE, SEQ ID NO:57) as well as SEQ ID NOs:34-35 and 54-97 in that publication. Additionally, 1T-6 (KFINGVLSQFVLERK, SEQ ID NO:58), 1T-18 (YSKTLHFAD, SEQ ID NO:59), 1T-30 (GKAK-PYQVRQVLRAVDKLETRRKKGGR, SEQ ID NO:60), PF-S024 (SKRGRKRKDRRKKKANHGKRPNS, SEQ ID NO:61) are can are suitable targeting peptides/domains. Other suitable targeting peptides are disclosed, for example, in priority documents U.S. Ser. No. 61/142,830, filed Jan. 6, 2009, U.S. Ser. No. 61/151,445, filed Feb. 10, 2009, U.S. Ser. No. 61/243,905, filed Sep. 18, 2009, and U.S. Ser. No. 61/243,930, filed Sep. 18, 2009.

In certain embodiments, targeting peptides consist of or comprise one or more of the *C. albicans* binding sequences shown in Table 6, or retro, inverse, retroinverso, or β forms thereof.

TABLE 6

Illustrative list of peptides that bind to *Candida albicans*.

| ID | Target(s) | Targeting Peptide Sequence | SEQ ID No. |
|---|---|---|---|
| PF-060 | hyphae | HSSHL | 62 |
| PF-024 | hyphae | DLRKAK | 63 |
| PF-636 | hyphae | LVRLA | 64 |
| PF-178 | hyphae | EVYSSPTNNVAITVQNN | 65 |
| PF-761 | hyphae | SKFELVNYASGCSCGADCKCASETECKCASKK | 66 |
| PF-770 | hyphae | GVGIGFIMMGVVGYAVKLVHIPIRYLIV | 67 |
| 1T-65 | hyphae | HARAAVGVAELPRGAAVEVELIAAVRP | 68 |
| PF-141 | hyphae | VVRRFQGM | 69 |
| PF-543 | hyphae | NILFGIIGFVVAMTAAVIVTAISIAK | 70 |
| PF-634 | hyphae | MPKARPVNHNKKKSKITIKSNFTLFYMFNP | 71 |
| PF-040 | hyphae | MIHLTKQNTMEALHFIKQFYDMFFILNFNV | 72 |
| PF-051 | hyphae | RFFNFEIKKSTKVDYVFAHVDLSDV | 73 |
| PF-580 | hyphae | EILNNNQVIKELTMKYKTQFESNLGGWTARARR | 74 |
| PF-583 | hyphae | KFQGEFTNIGQSYIVSASHMSTSLNTGK | 75 |
| 1T-36 | hyphae | VYRHLRFIDGKLVEIRLERK | 76 |
| PF-206 | hyphae | KLRSASKKSLQEKSCGIMPEKPAG | 77 |
| 1T-13 | yeast and hyphal forms | FRSPCINNNSLQPPGVYPAR | 78 |
| 1T-21 | yeast and hyphal forms | YVEEAVRAALKKEARISTEDTPVNLPSFDC | 79 |
| PF-030 | yeast and hyphal forms | MTCHQAPTTTHQSNMA | 80 |
| PF-463 | yeast and hyphal forms | MVILVFSLIFIFTDNYLVYQSKSIKEDVMI | 81 |
| PF-380 | yeast and hyphal forms | KKIIPLITLFVVTLVG | 82 |
| PF-515 | yeast and hyphal forms | DKSTQDKDIKQAKLLAQELGL-NH2 | 83 |
| PF-458 | yeast and hyphal forms | ISLIIFIMLFVVALFKCITNYKHQS | 85 |
| PF-S018 | yeast and hyphal forms | GMPQIPRLRI | 85 |
| 1T-16 | yeast and hyphal forms | IDMR | 86 |

TABLE 6-continued

Illustrative list of peptides that bind to *Candida albicans*.

| ID | Target(s) | Targeting Peptide Sequence | SEQ ID No. |
|---|---|---|---|
| PF-211 | yeast and hyphal forms | DSFDSLSPFRERGGEREDGCDAMPLP | 87 |
| PF-002 | yeast and hyphal forms | NDDAQ | 88 |
| PF-S003 | yeast and hyphal forms | ALALLKQDLLNFEGRGRIITSTYLQFNEGCVP | 89 |
| PF-021 | yeast and hyphal forms | FSLNFSKQKYVTVN | 90 |
| 1T-14 | yeast and hyphal forms | ALAGLAGLISGK | 91 |
| 1T-15 | yeast and hyphal forms | DVILRVEAQ | 92 |
| PF-629 | yeast and hyphal forms | GLAAIATVFALY | 93 |
| PF-617 | yeast and hyphal forms | PMNAAEPE | 94 |
| PF-621 | yeast and hyphal forms | PPSSFLV | 95 |
| PF-631 | yeast and hyphal forms | LIIYFSKTGNTARATRQI | 96 |
| PF-009 | yeast and hyphal forms | SKKYNHILNQENR | 97 |
| 1T-17 | yeast and hyphal forms | NNAIVYIS | 98 |
| 1T-20 | yeast and hyphal forms | PALVDLSNKEAVWAVLDDHS | 99 |
| 1T-68 | yeast cells | GGTKEIVYQRG | 100 |
| 1T-70 | yeast cells | NRQAQGERAHGEQQG | 101 |
| PF-167 | yeast cells | AIEGVIKKGACFKLLRHEMF | 102 |
| PF-168 | yeast cells | VLPFPAIPLSRRRACVAAPRPRSRQRAS | 103 |
| PF-170 | yeast cells | RLARGRPTNLCGRRG | 104 |
| PF-176 | yeast cells | RLTSNQFLTRITPFVFAQH | 105 |

The peptides in Table 6 were tested for binding efficiency at 3.13, 6.25, 12.5 and 25.0 µM concentrations in 1× phosphate-buffered saline or 20 mM HEPES (4-(2-hydroxyethyl)-1-piperazineethanesulfonic acid), 150 mM sodium chloride, 1 mM magnesium chloride and 0.1% CTAB.

Targeting Antibodies.

In certain embodiments the targeting moieties can comprise one or more antibodies that bind specifically or preferentially a microorganism or group of microorganisms (e.g., bacteria, fungi, yeasts, protozoa, viruses, algae, etc.). The antibodies are selected to bind an epitope characteristic or the particular target microorganism(s). In various embodiments such epitopes or antigens are typically is gram-positive or gram-negative specific, or genus-specific, or species-specific, or strain specific and located on the surface of a target microbial organism. The antibody that binds the epitope or antigen can direct an anti-microbial peptide moiety to the site. Furthermore, in certain embodiments the antibody itself can provide anti-microbial activity in addition to the activity provided by the AMP since the antibody may engage an immune system effector (e.g., a T-cell) and thereby elicit an antibody-associated immune response, e.g., a humoral immune response.

Antibodies that bind particular target microorganisms can be made using any methods readily available to one skilled in the art. For example, as described in U.S. Pat. No. 6,231,857 (incorporated herein by reference) three monoclonal antibodies, i.e., SWLA1, SWLA2, and SWLA3 have been made against *S. mutans*. Monoclonal antibodies obtained from non-human animals to be used in a targeting moiety can also be humanized by any means available in the art to decrease their immunogenicity and increase their ability to elicit anti-microbial immune response of a human Illustrative antibodies that bind various microorganisms are shown in Table 7.

TABLE 7

Illustrative antibodies that bind target microorganisms.

| Source | Antibody |
| --- | --- |
| U.S. Pat. No. 7,195,763 | Polyclonal/monoclonal binds specific Gram(+) cell wall repeats |
| U.S. Pat. No. 6,939,543 | Antibodies against G(+) LTA |
| U.S. Pat. No. 7,169,903 | Antibodies against G(+) peptidoglycan |
| U.S. Pat. No. 6,231,857 | Antibody against *S. mutans* (Shi) |
| U.S. Pat. No. 5,484,591 | Gram(−) binding antibodies |
| US 2007/0231321 | Diabody binding to *Streptococcus* surface antigen I/II |
| US 2003/0124635 | Antibody against *S. mutans* |
| US 2006/0127372 | Antibodies to *Actinomyces naeslundii*, *Lactobacillus casei* |
| US 2003/0092086 | Antibody to *S. sobrinus* |
| U.S. Pat. No. 7,364,738 | Monoclonal antibodies to the ClfA protein in *S. aureus* |
| U.S. Pat. No. 7,632,502 | Antibodies against *C. albicans* |
| U.S. Pat. No. 7,608,265 | Monoclonal against *C. difficile* |
| U.S. Pat. No. 4,777,136 | Monoclonal Antibodies against *Pseudomonas aeruginosa* |
| see, e.g., ab20429, ab20560, ab79522, ab35165, ab65602 from AbCAMm Cambridge Science Park, U.K. | Antibody against *S. pneumoniae* |

The targeting moiety can be attached directly to the AMP or compound AMP construct or it can be attached via a linker (e.g., as shown in Table 4).

AMPs Attached to Detectable Labels.

In certain embodiments chimeric moieties are provided comprising the antimicrobial peptides (e.g., peptides comprising one or more amino acid sequences found in Table 3) attached directly or through a linker to a detectable label. Such chimeric moieties are effective for detecting the presence and/or quantity, and/or location of the microorganism(s) that may be bound by the AMP(s). Similarly these chimeric moieties are useful to identify cells and/or tissues and/or food stuffs and/or other compositions that are infected with the targeted microorganism(s).

Detectable labels suitable for use in such chimeric moieties include any composition detectable by spectroscopic, photochemical, biochemical, immunochemical, electrical, optical, or chemical means. Illustrative useful labels include, but are not limited to, biotin for staining with labeled streptavidin conjugates, avidin or streptavidin for labeling with biotin conjugates fluorescent dyes (e.g., fluorescein, texas red, rhodamine, green fluorescent protein, and the like, see, e.g., Molecular Probes, Eugene, Oreg., USA), radiolabels (e.g., $^3$H, $^{125}$I, $^{35}$S, $^{14}$C, $^{32}$P, $^{99}$Tc, $^{203}$Pb, $^{67}$Ga, $^{68}$Ga, $^{72}$As, $^{111}$In, $^{113m}$In, $^{97}$Ru, $^{62}$Cu, $^{64}$lCu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{111}$Ag, and the like), enzymes (e.g., horse radish peroxidase, alkaline phosphatase and others commonly used in an ELISA), various colorimetric labels, magnetic or paramagnetic labels (e.g., magnetic and/or paramagnetic nanoparticles), spin labels, radio-opaque labels, and the like. Patents teaching the use of such labels include, for example, U.S. Pat. Nos. 3,817, 837; 3,850,752; 3,939,350; 3,996,345; 4,277,437; 4,275,149; and 4,366,241.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe—CdS core-shell nanocrystals enclosed in a silica shell can be easily derivatized for coupling to a biological molecule (Bruchez et al. (1998) *Science*, 281: 2013-2016). Similarly, highly fluorescent quantum dots (zinc sulfide-capped cadmium selenide) have been covalently coupled to biomolecules for use in ultrasensitive biological detection (Warren and Nie (1998) *Science*, 281: 2016-2018).

In various embodiments spin labels are provided by reporter molecules with an unpaired electron spin which can be detected by electron spin resonance (ESR) spectroscopy. Illustrative spin labels include organic free radicals, transitional metal complexes, particularly vanadium, copper, iron, and manganese, and the like. Exemplary spin labels include, for example, nitroxide free radicals.

Means of detecting such labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple colorimetric labels may be detected simply by observing the color associated with the label.

AMPS Attached to Targeting Enhancers/Opsonins

In certain embodiments compositions are contemplated that incorporate a targeting enhancer (e.g., an opsonin) attached to the AMP and/or to a targeted AMP. Targeting enhancers include moieties that increase binding affinity, and/or binding specificity, and/or internalization of a moiety by the target cell/microorganism.

Accordingly, in certain embodiments, an AMP and/or a targeted antimicrobial molecule is attached (e.g., conjugated) to an opsonin. When bound to a target cell through the targeting peptide, the opsonin component encourages phagocytosis and destruction by resident macrophages, dendritic cells, monocytes, or PMNs. Opsonins contemplated for conjugation can be of a direct or indirect type.

Direct opsonins include, fore example, any bacterial surface antigen, PAMP (pathogen-associated molecular pattern), or other molecule recognized by host PRRs (pathogen recognizing receptors). Opsonins can include, but are not limited to, bacterial protein, lipid, nucleic acid, carbohydrate and/or oligosaccharide moieties.

In certain embodiments opsonins include, but are not limited to, N-acetyl-D-glucosamine (GlcNAc), N-acetyl-D-galactosamine (GlaNAc), N-acetylglucosamine-containing muramyl peptides, NAG-muramyl peptides, NAG-NAM, peptidoglycan, teichoic acid, lipoteichoic acid, LPS, o-antigen, mannose, fucose, ManNAc, galactose, maltose, glucose, glucosamine, sucrose, mannosamine, galactose-alpha-1,3-galactosyl-beta-1,4-N-acetyl glucosamine, or alpha-1,3-gal-gal, or other sugars.

In certain embodiments, opsonins include indirect opsonins. Indirect opsonins function through binding to a direct opsonin already present. For example an Fc portion of an antibody, a sugar-binding lectin protein (example MBL), or host complement factors (example C3b, C4b, iC3b).

In certain embodiments the opsonin is to galactose-alpha-1,3-galactosyl-beta-1,4-N-acetyl glucosamine, or alpha-1,3-gal-gal.

Other examples of opsonin molecules include, but are not limited to antibodies (e.g., IgG and IgA), components of the complement system (e.g., C3b, C4b, and iC3b), mannose-binding lectin (MBL) (initiates the formation of C3b), and the like.

Methods of coupling an opsonin to a targeting moiety are well known to those of skill in the art (see, e.g., discussion below regarding attachment of effectors to targeting moieties).

III. Protecting Groups.

While the various peptides (e.g., targeted peptides, antimicrobial peptides, compound AMPs, etc.) described herein may be illustrated with no protecting groups, in certain embodiments they can bear one, two, three, four, or more protecting groups. In various embodiments, the protecting groups can be coupled to the C- and/or N-terminus of the peptide(s) and/or to one or more internal residues comprising the peptide(s) (e.g., one or more R-groups on the constituent amino acids can be blocked). Thus, for example, in certain embodiments, any of the peptides described herein can bear, e.g., an acetyl group protecting the amino terminus and/or an amide group protecting the carboxyl terminus. Illustrative examples of such a protected peptides include, but are not limited to: YIQFHLNQQPRPKVKKIKIFL-NH$_2$ (SEQ ID NO:3), WSRVPGHSDTGWKVWHRW-NH$_2$ (SEQ ID NO:8), RESKLIAMADMIRRRI-NH$_2$ (SEQ ID NO:11), LSEMERRRLRKRA-NH$_2$ (SEQ ID NO:4), FELVDWLET-NLGKILKSKSA-NH$_2$ (SEQ ID NO:27), and LGLT-AGVAYAAQPTNQPTNQPTNQPTNQPTNQPTNQPRW-NH$_2$ (SEQ ID NO:33). Of course, the —NH2 protecting group can be can be eliminated and/or substituted with another protecting group as described herein.

Without being bound by a particular theory, it was a discovered that addition of a protecting group, particularly to the carboxyl terminus, and/or in certain embodiments to the amino terminus, can improve the stability and efficacy of the peptide.

A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. In certain particularly preferred embodiments, the protecting groups include, but are not limited to alkyl chains as in fatty acids, propionyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g., groups having the formula: $CH_3—(CH_2)_n—CO—$ where n ranges from about 1 to about 20, preferably from about 1 to about 16 or 18, more preferably from about 3 to about 13, and most preferably from about 3 to about 10.

In certain embodiments, the acid group on the C-terminal can be blocked with an alcohol, aldehyde or ketone group and/or the N-terminal residue can have the natural amide group, or be blocked with an acyl, carboxylic acid, alcohol, aldehyde, or ketone group.

In certain embodiments, the protecting groups include, but are not limited to alkyl chains as in fatty acids, propionyl, formyl, and others. Particularly preferred carboxyl protecting groups include amides, esters, and ether-forming protecting groups. In one embodiment, an acetyl group is used to protect the amino terminus and/or an amino group is used to protect the carboxyl terminus (i.e., amidated carboxyl terminus). In certain embodiments blocking groups include alkyl groups of various lengths, e.g., groups having the formula: $CH_3—(CH_2)_n—CO—$ where n ranges from about 3 to about 20, preferably from about 3 to about 16, more preferably from about 3 to about 13, and most preferably from about 3 to about 10.

Other protecting groups include, but are not limited to Fmoc, t-butoxycarbonyl (t-BOC), 9-fluoreneacetyl group, 1-fluorenecarboxylic group, 9-fluorenecarboxylic group, 9-fluorenone-1-carboxylic group, benzyloxycarbonyl, xanthyl (Xan), trityl (Trt), 4-methyltrityl (Mtt), 4-methoxytrityl (Mmt), 4-methoxy-2,3,6-trimethyl-benzenesulphonyl (Mtr), mesitylene-2-sulphonyl (Mts), 4,4-dimethoxybenzhydryl (Mbh), tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimentyl-2,6-di-axocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), benzyloxymethyl (Bom), cyclohexyloxy (cHxO), t-butoxymethyl (Bum), t-butoxy (tBuO), t-Butyl (tBu), acetyl (Ac), and trifluoroacetyl (TFA).

Protecting/blocking groups are well known to those of skill as are methods of coupling such groups to the appropriate residue(s) comprising the peptides of this invention (see, e.g., Greene et al., (1991) *Protective Groups in Organic Synthesis, 2nd ed.*, John Wiley & Sons, Inc. Somerset, N.J.). In illustrative embodiment, for example, acetylation is accomplished during the synthesis when the peptide is on the resin using acetic anhydride. Amide protection can be achieved by the selection of a proper resin for the synthesis. For example, a rink amide resin can be used. After the completion of the synthesis, the semipermanent protecting groups on acidic bifunctional amino acids such as Asp and Glu and basic amino acid Lys, hydroxyl of Tyr are all simultaneously removed. The peptides released from such a resin using acidic treatment comes out with the n-terminal protected as acetyl and the carboxyl protected as NH$_2$ and with the simultaneous removal of all of the other protecting groups.

Where amino acid sequences are disclosed herein, amino acid sequences comprising, one or more protecting groups, e.g., as described above (or any other commercially available protecting groups for amino acids used, e.g., in boc or fmoc peptide synthesis) are also contemplated.

IV. Peptide Preparation.

The peptides described herein can be chemically synthesized using standard chemical peptide synthesis techniques or, particularly where the peptide does not comprise "D" amino acid residues, the peptide can be recombinantly expressed. Where the "D" polypeptides are recombinantly expressed, a host organism (e.g. bacteria, plant, fungal cells, etc.) can be cultured in an environment where one or more of the amino acids is provided to the organism exclusively in a D form. Recombinantly expressed peptides in such a system then incorporate those D amino acids.

In certain embodiments, D amino acids can be incorporated in recombinantly expressed peptides using modified amino acyl-tRNA synthetases that recognize D-amino acids.

Chemical Synthesis.

In certain embodiments the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides of this invention. Techniques for solid phase synthesis are well known to those of skill in the art and are described, for example, by Barany and Merrifield (1963) *Solid-Phase Peptide Synthesis*; pp. 3-284 in *The Peptides: Analysis, Synthesis, Biology. Vol. 2: Special Methods in Peptide Synthesis, Part A.*; Merrifield et al. (1963) *J. Am. Chem. Soc.*, 85: 2149-2156, and Stewart et al. (1984) *Solid Phase Peptide Synthesis,* 2nd ed. Pierce Chem. Co., Rockford, Ill.

In one illustrative embodiment, the peptides can be synthesized by the solid phase peptide synthesis procedure using a benzhyderylamine resin (Beckman Bioproducts, 0.59 mmol of $NH_2$/g of resin) as the solid support. The COOH terminal amino acid (e.g., t-butylcarbonyl-Phe) is attached to the solid support through a 4-(oxymethyl)phenacetyl group. This is a more stable linkage than the conventional benzyl ester linkage, yet the finished peptide can still be cleaved by hydrogenation. Transfer hydrogenation using formic acid as the hydrogen donor can be used for this purpose.

It is noted that in the chemical synthesis of peptides, particularly peptides comprising D amino acids, the synthesis usually produces a number of truncated peptides in addition to the desired full-length product. Thus, the peptides are typically purified using, e.g., HPLC.

D-amino acids, beta amino acids, non-natural amino acids, and the like can be incorporated at one or more positions in the peptide simply by using the appropriately derivatized amino acid residue in the chemical synthesis. Modified residues for solid phase peptide synthesis are commercially available from a number of suppliers (see, e.g., Advanced Chem Tech, Louisville; Nova Biochem, San Diego; Sigma, St Louis; Bachem California Inc., Torrance, etc.). The D-form and/or otherwise modified amino acids can be completely omitted or incorporated at any position in the peptide as desired. Thus, for example, in certain embodiments, the peptide can comprise a single modified acid, while in other embodiments, the peptide comprises at least two, generally at least three, more generally at least four, most generally at least five, preferably at least six, more preferably at least seven or even all modified amino acids. In certain embodiments, essentially every amino acid is a D-form amino acid.

Recombinant Expression.

As indicated above, the antimicrobial peptides can also be recombinantly expressed. Accordingly, in certain embodiments, the antimicrobial peptides and/or targeting moieties, and/or fusion proteins of this invention are synthesized using recombinant expression systems. Generally this involves creating a DNA sequence that encodes the desired peptide or fusion protein, placing the DNA in an expression cassette under the control of a particular promoter, expressing the peptide or fusion protein in a host, isolating the expressed peptide or fusion protein and, if required, renaturing the peptide or fusion protein.

DNA encoding the peptide(s) or fusion protein(s) described herein can be prepared by any suitable method as described above, including, for example, cloning and restriction of appropriate sequences or direct chemical synthesis.

This nucleic acid can be easily ligated into an appropriate vector containing appropriate expression control sequences (e.g. promoter, enhancer, etc.), and, optionally, containing one or more selectable markers (e.g. antibiotic resistance genes).

The nucleic acid sequences encoding the peptides or fusion proteins described herein can be expressed in a variety of host cells, including, but not limited to, *E. coli*, other bacterial hosts, yeast, fungus, and various higher eukaryotic cells such as insect cells (e.g. SF3), the COS, CHO and HeLa cells lines and myeloma cell lines. The recombinant protein gene will typically be operably linked to appropriate expression control sequences for each host. For *E. coli* this can include a promoter such as the T7, trp, or lambda promoters, a ribosome binding site and preferably a transcription termination signal. For eukaryotic cells, the control sequences can include a promoter and often an enhancer (e.g., an enhancer derived from immunoglobulin genes, SV40, cytomegalovirus, etc.), and a polyadenylation sequence, and may include splice donor and acceptor sequences.

The plasmids can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as amp, gpt, neo, hyg, and the like.

Once expressed, the recombinant peptide(s) or fusion protein(s) can be purified according to standard procedures of the art, including ammonium sulfate precipitation, affinity columns, column chromatography, gel electrophoresis and the like (see, generally, R. Scopes, (1982) *Protein Purification*, Springer-Verlag, N.Y.; Deutscher (1990) *Methods in Enzymology Vol. 182: Guide to Protein Purification.*, Academic Press, Inc. N.Y.). Substantially pure compositions of at least about 90 to 95% homogeneity are preferred, and 98 to 99% or more homogeneity are most preferred.

One of skill in the art would recognize that after chemical synthesis, biological expression, or purification, the peptide(s) or fusion protein(s) may possess a conformation substantially different than desired native conformation. In this case, it may be necessary to denature and reduce the peptide or fusion protein and then to cause the molecule to re-fold into the preferred conformation. Methods of reducing and denaturing proteins and inducing re-folding are well known to those of skill in the art (see, e.g., Debinski et al. (1993) *J. Biol. Chem.*, 268: 14065-14070; Kreitman and Pastan (1993) *Bioconjug. Chem.*, 4: 581-585; and Buchner, et al., (1992) *Anal. Biochem.*, 205: 263-270). Debinski et al., for example, describes the denaturation and reduction of inclusion body proteins in guanidine-DTE. The protein is then refolded in a redox buffer containing oxidized glutathione and L-arginine.

One of skill would recognize that modifications can be made to the peptide(s) and/or fusion protein(s) proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Attachment of AMPs to Each Other and/or to a Targeting Moiety, Detectable Label and/or Opsonin.

Chemical Conjugation.

Chimeric moieties are formed by joining one or more of the AMPs moieties described herein to each other and/or to one or more targeting moieties and/or to detectable labels and/or to opsonins. In certain embodiments the components are attached directly to each other via naturally occurring reactive groups or the AMPs and/or targeting moieties can be functionalized to provide such reactive groups.

In various embodiments the AMPs are attached to each other and/or to targeting moieties via one or more linking agents. Thus, in various embodiments the AMPs and/or targeting moieties can be conjugated via a single linking agent or multiple linking agents. For example, they can be conjugated via a single multifunctional (e.g., bi-, tri-, or tetra-) linking agent or a pair of complementary linking agents. In another embodiment, the AMPs and/or targeting moieties are conjugated via two, three, or more linking agents. Suitable linking agents include, but are not limited to, e.g., functional groups, affinity agents, stabilizing groups, and combinations thereof.

In certain embodiments the linking agent is or comprises a functional group. Functional groups include monofunctional linkers comprising a reactive group as well as multifunctional crosslinkers comprising two or more reactive groups capable of forming a bond with two or more different functional targets (e.g., labels, proteins, macromolecules, semiconductor nanocrystals, or substrate). In some preferred embodiments, the multifunctional crosslinkers are heterobifunctional crosslinkers comprising two or more different reactive groups.

Suitable reactive groups include, but are not limited to thiol (—SH), carboxylate (COOH), carboxyl (—COOH), carbonyl, amine ($NH_2$), hydroxyl (—OH), aldehyde (—CHO), alcohol (ROH), ketone ($R_2CO$), active hydrogen, ester, sulfhydryl (SH), phosphate (—$PO_3$), or photoreactive moieties. Amine reactive groups include, but are not limited to e.g., isothiocyanates, isocyanates, acyl azides, NHS esters, sulfonyl chlorides, aldehydes and glyoxals, epoxides and oxiranes, carbonates, arylating agents, imidoesters, carbodiimides, and anhydrides. Thiol-reactive groups include, but are not limited to e.g., haloacetyl and alkyl halide derivates, maleimides, aziridines, acryloyl derivatives, arylating agents, and thiol-disulfides exchange reagents. Carboxylate reactive groups include, but are not limited to e.g., diazoalkanes and diazoacetyl compounds, such as carbonyldiimidazoles and carbodiimides. Hydroxyl reactive groups include, but are not limited to e.g., epoxides and oxiranes, carbonyldiimidazole, oxidation with periodate, N,N'-disuccinimidyl carbonate or N-hydroxylsuccimidyl chloroformate, enzymatic oxidation, alkyl halogens, and isocyanates. Aldehyde and ketone reactive groups include, but are not limited to e.g., hydrazine derivatives for schiff base formation or reduction amination. Active hydrogen reactive groups include, but are not limited to e.g., diazonium derivatives for mannich condensation and iodination reactions. Photoreactive groups include, but are not limited to e.g., aryl azides and halogenated aryl azides, benzophenones, diazo compounds, and diazirine derivatives.

Other suitable reactive groups and classes of reactions useful in forming chimeric moieties include those that are well known in the art of bioconjugate chemistry. Currently favored classes of reactions available with reactive chelates are those which proceed under relatively mild conditions. These include, but are not limited to, nucleophilic substitutions (e.g., reactions of amines and alcohols with acyl halides, active esters), electrophilic substitutions (e.g., enamine reactions), and additions to carbon-carbon and carbon-heteroatom multiple bonds (e.g., Michael reaction, Diels-Alder addition). These and other useful reactions are discussed in, for example, March (1985) *Advanced Organic Chemistry*, 3rd Ed., John Wiley & Sons, New York, Hermanson (1996) *Bioconjugate Techniques*, Academic Press, San Diego; and Feeney et al. (1982) *Modification of Proteins; Advances in Chemistry Series*, Vol. 198, American Chemical Society, Washington, D.C.

A "linker" or "linking agent" as used herein, is a molecule that is used to join two or more molecules. In certain embodiments the linker is typically capable of forming covalent bonds to both molecule(s) (e.g., the targeting moiety and the effector). Suitable linkers are well known to those of skill in the art and include, but are not limited to, straight or branched-chain carbon linkers, heterocyclic carbon linkers, or peptide linkers. In certain embodiments the linkers can be joined to the constituent amino acids through their side groups (e.g., through a disulfide linkage to cysteine). However, in certain embodiments, the linkers will be joined to the alpha carbon amino and carboxyl groups of the terminal amino acids. An list of suitable linkers is shown in Table 4.

A bifunctional linker having one functional group reactive with a group on one molecule (e.g., a targeting peptide), and another group reactive on the other molecule (e.g., an antimicrobial peptide), can be used to form the desired conjugate. Alternatively, derivatization can be performed to provide functional groups. Thus, for example, procedures for the generation of free sulfhydryl groups on peptides are also known (See U.S. Pat. No. 4,659,839).

In certain embodiments the linking agent is a heterobifunctional crosslinker comprising two or more different reactive groups that form a heterocyclic ring that can interact with a peptide. For example, a heterobifunctional crosslinker such as cysteine may comprise an amine reactive group and a thiol-reactive group can interact with an aldehyde on a derivatized peptide. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups. In one embodiment, the heterobifunctional crosslinker is SMCC.

Many procedures and linker molecules for attachment of various molecules to peptides or proteins are known (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075). Illustrative linking protocols are provided herein in Examples 2 and 3.

Fusion Proteins.

In certain embodiments where the moieties to be joined (AMPs and/or targeting moieties) are all peptides, the chimeric moiety can be chemically synthesized or recombinantly expressed as a fusion protein (i.e., a chimeric fusion protein).

In certain embodiments the chimeric fusion proteins are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein e.g., as described above.

Peptide Circularization.

In certain embodiments the peptides described herein (e.g., AMPs, compound AMPs, etc.) are circularized to produce cyclic peptides. Cyclic peptides, as contemplated herein, include head/tail, head/side chain, tail/side chain, and side chain/side chain cyclized peptides. In addition, peptides contemplated herein include homodet, containing only peptide bonds, and heterodet containing in addition disulfide, ester, thioester-bonds, or other bonds.

The cyclic peptides can be prepared using virtually any art-known technique for the preparation of cyclic peptides. For example, the peptides can be prepared in linear or non-cyclized form using conventional solution or solid phase peptide syntheses and cyclized using standard chemistries. Preferably, the chemistry used to cyclize the peptide will be sufficiently mild so as to avoid substantially degrading the peptide. Suitable procedures for synthesizing the peptides described herein as well as suitable chemistries for cyclizing the peptides are well known in the art.

In various embodiments cyclization can be achieved via direct coupling of the N- and C-terminus to form a peptide (or other) bond, but can also occur via the amino acid side chains. Furthermore it can be based on the use of other functional groups, including but not limited to amino, hydroxy, sulfhydryl, halogen, sulfonyl, carboxy, and thiocarboxy. These groups can be located at the amino acid side chains or be attached to their N- or C-terminus.

Accordingly, it is to be understood that the chemical linkage used to covalently cyclize the peptides of the invention need not be an amide linkage. In many instances it may be desirable to modify the N- and C-termini of the linear or non-cyclized peptide so as to provide, for example, reactive groups that may be cyclized under mild reaction conditions. Such linkages include, by way of example and not limitation amide, ester, thioester, $CH_2$—NH, etc. Techniques and reagents for synthesizing peptides having modified termini and chemistries suitable for cyclizing such modified peptides are well-known in the art.

Alternatively, in instances where the ends of the peptide are conformationally or otherwise constrained so as to make cyclization difficult, it may be desirable to attach linkers to the N- and/or C-termini to facilitate peptide cyclization. Of course, it will be appreciated that such linkers will bear reactive groups capable of forming covalent bonds with the termini of the peptide. Suitable linkers and chemistries are well-known in the art and include those previously described.

Cyclic peptides and depsipeptides (heterodetic peptides that include ester (depside) bonds as part of their backbone) have been well characterized and show a wide spectrum of biological activity. The reduction in conformational freedom brought about by cyclization often results in higher receptor-binding affinities. Frequently in these cyclic compounds, extra conformational restrictions are also built in, such as the use of D- and N-alkylated-amino acids, α,β-dehydro amino acids or α,α-disubstituted amino acid residues.

Methods of forming disulfide linkages in peptides are well known to those of skill in the art (see, e.g., Eichler and Houghten (1997) *Protein Pept. Lett.* 4: 157-164).

Reference may also be made to Marlowe (1993) *Biorg. Med. Chem. Lett.* 3: 437-44 who describes peptide cyclization on TFA resin using trimethylsilyl (TMSE) ester as an orthogonal protecting group; Pallin and Tam (1995) *J. Chem. Soc. Chem. Comm.* 2021-2022) who describe the cyclization of unprotected peptides in aqueous solution by oxime formation; Algin et al. (1994) *Tetrahedron Lett.* 35: 9633-9636 who disclose solid-phase synthesis of head-to-tail cyclic peptides via lysine side-chain anchoring; Kates et al. (1993) *Tetrahedron Lett.* 34: 1549-1552 who describe the production of head-to-tail cyclic peptides by three-dimensional solid phase strategy; Tumelty et al. (1994) *J. Chem. Soc. Chem. Comm.* 1067-1068, who describe the synthesis of cyclic peptides from an immobilized activated intermediate, where activation of the immobilized peptide is carried out with N-protecting group intact and subsequent removal leading to cyclization; McMurray et al. (1994) *Peptide Res.* 7: 195-206) who disclose head-to-tail cyclization of peptides attached to insoluble supports by means of the side chains of aspartic and glutamic acid; Hruby et al. (1994) *Reactive Polymers* 22: 231-241) who teach an alternate method for cyclizing peptides via solid supports; and Schmidt and Langer (1997) *J. Peptide Res.* 49: 67-73, who disclose a method for synthesizing cyclotetrapeptides and cyclopentapeptides.

These methods of peptide cyclization are illustrative and non-limiting. Using the teaching provide herein, other cyclization methods will be available to one of skill in the art.

V. Identification/Verification of Active Peptides

The active AMPs and AMP constructs can be identified and/or validated using an in vitro screening assay. Indeed, in many instances the AMPs described herein will be used in vitro as preservatives, topical antimicrobial treatments, and the like. Additionally, despite certain apparent limitations of in vitro susceptibility tests, clinical data indicate that a good correlation exists between minimal inhibitory concentration (MIC) test results and in vivo efficacy of antibiotic compounds (see, e.g., Murray et al. (1994) Antimicrobial Susceptibility Testing, Poupard et al., eds., Plenum Press, New York; Knudsen et al. (1995) *Antimicrob. Agents Chemother.* 39(6): 1253-1258; and the like). Thus, AMPs useful for treating infections and diseases related thereto are also conveniently identified by demonstrated in vitro antimicrobial activity against specified microbial targets, e.g., as illustrated in Table 3).

Typically, the in vitro antimicrobial activity of antimicrobial agents is tested using standard NCCLS bacterial inhibition assays, or MIC tests (see, National Committee on Clinical Laboratory Standards "Performance Standards for Antimicrobial Susceptibility Testing," NCCLS Document M100-S5 Vol. 14, No. 16, December 1994; "Methods for dilution antimicrobial susceptibility test for bacteria that grow aerobically-Third Edition," Approved Standard M7-A3, National Committee for Clinical Standards, Villanova, Pa.).

In certain embodiments the MIC assays are performed as described herein in the Examples. For each organism, the media and growth conditions utilized is detailed in Table 8. MIC tests were conducted in 96-well plates with 100 μL of bacterial or yeast suspension added in each well and challenged with twofold serial dilutions of peptide starting at 50 μM. After incubation 18-24 h, or in some cases 48 h, the lowest concentration at which the peptide inhibited bacterial and/or fungal growth was noted as the MIC (observation of a clear well by visual inspection).

TABLE 8

List of organisms, growth conditions and starting inoculum concentrations

| Organism | Medium | Growth conditions | Starting inoculum (CFU/ml) |
|---|---|---|---|
| A. baumannii | LB | 30° C., anaerobic | $10^5$ |
| A. naeslundii | Columbia broth | 37° C., anaerobic | $10^5$ |
| A. niger | Potato Dextrose Agar | 25° C., aerobic | $10^5$ |
| B. subtilis | BHI | 30° C., aerobic | $10^5$ |
| C. albicans | MH | 37° C., aerobic | $10^5$ |
| C. difficile | BHIS | 37° C., anaerobic | $10^5$ |
| C. jeikeium | TSB supplemented with 1% Tween-80 | 37° C., aerobic | $10^6$ |
| E. faecalis | TSB supplemented with 1% glucose | 37° C., aerobic | $10^5$ |
| E. coli | LB | 37° C., aerobic | $10^5$ |
| F. nucleatum | Columbia broth | 37° C., anaerobic | $10^5$ |
| M. furfur | ATCC medium 1072 | 37° C., aerobic | $10^5$ |
| P. gingivalis | Columbia broth | 37° C., anaerobic | $10^5$ |
| P. aeruginosa | MH | 37° C., aerobic | $10^5$ |
| S. aureus MRSA | BHI supplemented with 2% glucose | 37° C., aerobic | $10^5$ |
| S. epidermidis | BHI supplemented with 0.25% glucose | 37° C., aerobic | $10^5$ |
| S. mutans | TH supplemented with 1% sucrose | 37° C., anaerobic | $10^5$ |

TABLE 8-continued

List of organisms, growth conditions and starting inoculum concentrations

| Organism | Medium | Growth conditions | Starting inoculum (CFU/ml) |
|---|---|---|---|
| S. pneumoniae | TSB supplemented with 5% yeast extract | 37° C., 10% CO2 | $10^6$ |
| T. rubrum | Potato Dextrose Agar | 25° C., aerobic | $10^5$ |

It will be appreciated that other assays as are well known in the art or that will become apparent to those having skill in the art upon review of this disclosure may also be used to identify active AMPs. Such assays include, for example, the assay described in Lehrer et al. (1988) *J. Immunol. Meth.*, 108: 153 and Steinberg and Lehrer, "Designer Assays for Antimicrobial Peptides: Disputing the 'One Size Fits All' Theory," In: Antibacterial Peptide Protocols, Shafer, Ed., Humana Press, N.J. Generally, active peptides of the invention will exhibit MICs (as measured using the assays described in the examples) of less than about 100 µM, preferably less than about 80 or 60 µM, more preferably about 50 µM or less, about 25 µM or less, or about 15 µM or less, or about 10 µM or less.

VI. Formulations.

Pharmaceutical Formulations.

In certain embodiments one or more active agents (e.g., antimicrobial peptides (AMPs) or compound antimicrobial peptides described herein) are administered to a mammal in need thereof, e.g., to a mammal suffering from a microbial infection (e.g., bacterial or fungal infection) or prophylactically to prevent a microbial infection and/or to prevent or reduce the incidence or severity of dental caries.

The active agent(s) can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure*, 4th Ed. N.Y. Wiley-Interscience.

Methods of formulating such derivatives are known to those of skill in the art. For example, the disulfide salts of a number of delivery agents are described in PCT Publication WO 2000/059863. Similarly, acid salts of therapeutic peptides, peptoids, or other mimetics, and can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

For the preparation of salt forms of basic drugs, the pKa of the counterion is preferably at least about 2 pH lower than the pKa of the drug. Similarly, for the preparation of salt forms of acidic drugs, the pKa of the counterion is preferably at least about 2 pH higher than the pKa of the drug. This permits the counterion to bring the solution's pH to a level lower than the pHmax to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of Esters Typically Involves Functionalization of Hydroxyl and/or carboxyl groups that are present within the molecular structure of the active agent. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the active agents identified herein are useful for parenteral, topical, oral, nasal (or otherwise inhaled), rectal, or local administration, such as by aerosol or transdermally, for prophylactic and/or therapeutic treatment of infection (e.g., microbial infection) one or more of the pathologies/indications described herein (e.g., atherosclerosis and/or symptoms thereof).

The active agents of this invention can also be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds, particularly of use in the preparation of tablets, capsules, gel caps, and the like include, but are not limited to binders, diluent/fillers, disentegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g., active peptide and salicylanilide) and the resulting composition is compressed. Where necessary the compressed product is coated, e.g., known methods for masking the taste or for enteric dissolution or sustained release. Suitable coating materials include, but are not limited to ethyl-cellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectables, implantable sustained-release formulations, mucoadherent films, topical varnishes, lipid complexes, etc.

Pharmaceutical compositions comprising the peptides described herein can be manufactured by means of conventional mixing, dissolving, granulating, dragee-making, levigating, emulsifying, encapsulating, entrapping or lyophilizing processes. Pharmaceutical compositions can be formulated in a conventional manner using one or more physiologically acceptable carriers, diluents, excipients or auxiliaries that facilitate processing of the active peptides into preparations which can be used pharmaceutically. Proper formulation is dependent upon the route of administration chosen.

For topical administration the peptides of the invention may be formulated as solutions, gels, ointments, creams, suspensions, and the like as are well-known in the art. Systemic formulations include, but are not limited to, those designed for administration by injection, e.g. subcutaneous, intravenous, intramuscular, intrathecal or intraperitoneal injection, as well as those designed for transdermal, transmucosal oral or pulmonary administration. For injection, the active agents described herein can be formulated in aqueous solutions, preferably in physiologically compatible buffers such as Hanks solution, Ringer's solution, or physiological saline buffer and/or in certain emulsion formulations. The solution can contain formulatory agents such as suspending, stabilizing and/or dispersing agents. In certain embodiments the active agent(s) can be provided in powder form for constitution with a suitable vehicle, e.g., sterile pyrogen-free water, before use. For transmucosal administration, penetrants appropriate to the barrier to be permeated can be used in the formulation. Such penetrants are generally known in the art.

For oral administration, the compounds can be readily formulated by combining the active agent(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like can be added. For buccal administration, the compositions may take the form of tablets, lozenges, etc. formulated in conventional manner.

For administration by inhalation, the active agent(s) are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

In various embodiments the active agent(s) can be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations can be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides of the invention. Certain organic solvents such as dimethylsulfoxide also can be employed, although usually at the cost of greater toxicity. Additionally, the compounds may be delivered using a sustained-release system, such as semi-permeable matrices of solid polymers containing the therapeutic agent. Various uses of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

In certain embodiments, the active agents of this invention are administered to the oral cavity. This is readily accomplished by the use of lozenges, aerosol sprays, mouthwash, coated swabs, and the like.

In certain embodiments, the active agent(s) of this invention are administered topically, e.g., to the skin surface, to a topical lesion or wound, to a surgical site, and the like.

In certain embodiments the active agents of this invention are administered systemically (e.g., orally, or as an injectable) in accordance with standard methods well known to those of skill in the art. In other preferred embodiments, the agents, can also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other formulations for topical delivery include, but are not limited to, ointments, gels, sprays, fluids, and creams. Ointments are semisolid preparations that are typically based on petrolatum or other petroleum derivatives. Creams containing the selected active agent are typically viscous liquid or semi-solid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and non-sensitizing.

As indicated above, various buccal, and sublingual formulations are also contemplated.

In certain embodiments, one or more active agents of the present invention can be provided as a "concentrate", e.g., in a storage container (e.g., in a premeasured volume) ready for dilution, or in a soluble capsule ready for addition to a volume of water, alcohol, hydrogen peroxide, or other diluent.

While the invention is described with respect to use in humans, it is also suitable for animal, e.g., veterinary use. Thus certain preferred organisms include, but are not limited to humans, non-human primates, canines, equines, felines, porcines, ungulates, largomorphs, and the like.

The foregoing formulations and administration methods are intended to be illustrative and not limiting. It will be appreciated that, using the teaching provided herein, other suitable formulations and modes of administration can be readily devised.

Home Health Care Product Formulations.

In certain embodiments, one or more of the antimicrobial peptides (AMPs) and/or compound AMPs of the present invention are incorporated into healthcare formulations, e.g., for home use. Such formulations include, but are not limited to toothpaste, mouthwash, tooth whitening strips or solutions, contact lens storage, wetting, or cleaning solutions, dental floss, toothpicks, toothbrush bristles, oral sprays, oral lozenges, nasal sprays, aerosolizers for oral and/or nasal application, wound dressings (e.g., bandages), and the like.

The formulation of such health products is well known to those of skill, and the AMPs and/or compound AMPs of the present invention are simply added to such formulations in an effective dose (e.g., a prophylactic dose to inhibit dental carie formation, etc.).

For example, toothpaste formulations are well known to those of skill in the art. Typically such formulations are mixtures of abrasives and surfactants; anticaries agents, such as fluoride; tartar control ingredients, such as tetrasodium pyrophosphate and methyl vinyl ether/maleic anhydride copolymer; pH buffers; humectants, to prevent dry-out and increase the pleasant mouth feel; and binders, to provide consistency and shape (see, e.g., Table 9). Binders keep the solid phase properly suspended in the liquid phase to prevent separation of the liquid phase out of the toothpaste. They also provide body to the dentifrice, especially after extrusion from the tube onto the toothbrush.

TABLE 9

Typical components of toothpaste.

| Ingredients | Wt % |
|---|---|
| Humectants | 40-70 |
| Water | 0-50 |
| Buffers/salts/tartar control | 0.5-10 |
| Organic thickeners (gums) | 0.4-2 |
| Inorganic thickeners | 0-12 |

TABLE 9-continued

Typical components of toothpaste.

| Ingredients | Wt % |
|---|---|
| Abrasives | 10-50 |
| Actives (e.g., triclosan) | 0.2-1.5 |
| Surfactants | 0.5-2 |
| Flavor and sweetener | 0.8-1.5 |

Fluoride sources provide 1000-15000 ppm fluorine.

Table 10 lists typical ingredients used in formulations; the final combination will depend on factors such as ingredient compatibility and cost, local customs, and desired benefits and quality to be delivered in the product. It will be recognized that one or more AMPs and/or compound AMPs of the present invention can simply be added to such formulations or used in place of one or more of the other ingredients.

TABLE 10

List of typical ingredients.

| Gums | Inorganic Thickeners | Abrasives | Surfactants | Humectants | Tartar Control Ingredient |
|---|---|---|---|---|---|
| Sodium carboxymethyl cellulose | Silica thickeners | Hydrated silica | Sodium lauryl sulfate | Glycerine | Tetrasodium pyrophosphate |
| Cellulose ethers | Sodium aluminum silicates | Dicalcium phosphate digydrate | Sodium N-lauryl sarcosinate | Sorbitol | Gantrez S-70 |
| Xanthan Gum | Clays | Calcium carbonate | Pluronics | Propylene glycol | Sodium tri-polyphosphate |
| Carrageenans | | Sodium bicarbonate | | Xylitol | |
| Sodium alginate | | Calcium pyrophosphate | Sodium lauryl sulfoacetate | Polyethylene glycol | |
| Carbopols | | Alumina | | | |

One illustrative formulation described in U.S. Pat. No. 6,113,887 comprises (1) a water-soluble bactericide selected from the group consisting of pyridinium compounds, quaternary ammonium compounds and biguanide compounds in an amount of 0.001% to 5.0% by weight, based on the total weight of the composition; (2) a cationically-modified hydroxyethylcellulose having an average molecular weight of 1,000,000 or higher in the hydroxyethylcellulose portion thereof and having a cationization degree of 0.05 to 0.5 mol/glucose in an amount of 0.5% to 5.0% by weight, based on the total weight of the composition; (3) a surfactant selected from the group consisting of polyoxyethylene polyoxypropylene block copolymers and alkylolamide compounds in an amount of 0.5% to 13% by weight, based on the total weight of the composition; and (4) a polishing agent of the non-silica type in an amount of 5% to 50% by weight, based on the total weight of the composition. In certain embodiments, the AMPs and/or compound AMPs of this invention can be used in place of the bactericide or in combination with the bactericide.

Similarly, mouthwash formulations are also well known to those of skill in the art. Thus, for example, mouthwashes containing sodium fluoride are disclosed in U.S. Pat. Nos. 2,913,373, 3,975,514, and 4,548,809, and in US Patent Publications US 2003/0124068 A1, US 2007/0154410 A1, and the like. Mouthwashes containing various alkali metal compounds are also known: sodium benzoate (WO 9409752); alkali metal hypohalite (US 20020114851A1); chlorine dioxide (CN 1222345); alkali metal phosphate (US 2001/0002252 A1, US 2003/0007937 A1); hydrogen sulfate/carbonate (JP 8113519); cetylpyridium chloride (CPC) (see, e.g., U.S. Pat. No. 6,117,417, U.S. Pat. No. 5,948,390, and JP 2004051511). Mouthwashes containing higher alcohol (see, e.g., US 2002/0064505 A1, US 2003/0175216 A1); hydrogen peroxide (see, e.g., CN 1385145); $CO_2$ gas bubbles (see, e.g., JP 1275521 and JP 2157215) are also known. In certain embodiments, these and other mouthwash formulations can further comprise one or more of the AMPs or compound AMPs of this invention.

Contact lens storage, wetting, or cleaning solutions, deodorants, dental floss, toothpicks, toothbrush bristles, oral sprays, oral lozenges, nasal sprays, and aerosolizers for oral and/or nasal application, and the like are also well known to those of skill in the art and can readily be adapted to incorporate one or more AMPs and/or compound AMPs of the present invention.

The foregoing home healthcare formulations and/or devices are meant to be illustrative and not limiting. Using teaching provided herein, the AMPs and/or compound AMPs of the present invention can readily be incorporated into other products.

Effective Dosages

The AMPs compound AMPs and other constructs described herein will generally be used in an amount effective to achieve the intended purpose. Of course, it is to be understood that the amount used will depend on the particular application. For example, for use as a disinfectant or preservative, an antimicrobially effective amount of an antimicrobial peptide, or composition thereof, is applied or added to the material to be disinfected or preserved. By antimicrobially effective amount is meant an amount of peptide or composition that inhibits the growth and/or proliferation of, or is lethal to, a target microbe population. While the actual antimicrobially effective amount will depend on a particular application, for use as a disinfectant or preservative the peptides, or compositions thereof, are usually added or applied to the material to be disinfected or preserved in relatively low amounts. Typically, the peptide comprises less than about 20%, 15%, 10%, or 5% by weight of the disinfectant solution or material to be preserved, preferably less than about 1% by weight and more preferably less than about 0.1% by weight. An ordinarily skilled artisan will be able to determine antimicrobially effective amounts of particular peptides for particular applications without undue experimentation using, for example, the in vitro assays provided in the examples.

In certain therapeutic applications, the compositions of this invention are administered, e.g., topically administered or administered to the oral or nasal cavity, to a patient suffering from infection or at risk for infection or prophylactically to prevent infection. In certain embodiments the administration is to prevent dental caries and/or periodontal disease, and/or other pathologies of the teeth or oral mucosa characterized by microbial infection.

More generally, the composition (e.g., AMP, compound AMP, etc.) is administered therapeutically to kill and/or to inhibit the growth and/or proliferation of a microorganism and/or a biofilm comprising one or more microorganisms. Similarly the composition can be administered prophylactically to reduce the infectivity of a microorganism and/or to prevent/inhibit the growth and/or proliferation of a microorganism and/or a biofilm comprising the microorganism.

An amount adequate to kill and/or inhibit the growth and/or proliferation of a microorganism or sufficient to prevent and/or cure and/or at least partially prevent or arrest a disease and/or its complications is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms in) the patient.

The concentration of active agent(s) can vary widely, and will be selected primarily based on activity of the active ingredient(s), body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. In certain embodiments, dosages range from about 20 mg to about 50 mg given orally twice daily. It will be appreciated that such dosages may be varied to optimize a therapeutic and/or phophylactic regimen in a particular subject or group of subjects. Determination of a therapeutically effective amount is well within the capabilities of those skilled in the art, especially in light of the detailed disclosure provided herein.

As in the case of disinfectants and preservatives, for topical administration to treat or prevent bacterial, yeast, fungal or other infections a therapeutically effective dose can be determined using, for example, the in vitro assays provided in the examples. The treatment may be applied while the infection is visible, or even when it is not visible. An ordinarily skilled artisan will be able to determine therapeutically effective amounts to treat topical infections without undue experimentation.

For systemic administration, a therapeutically effective dose can be estimated initially from in vitro assays. For example, a dose can be formulated in animal models to achieve a circulating cyclic peptide concentration range that includes the $I_{50}$ as determined in cell culture (i.e., the concentration of test compound that is lethal to 50% of a cell culture), the MIC, as determined in cell culture (i.e., the minimal inhibitory concentration for growth) or the $I_{100}$ as determined in cell culture (i.e., the concentration of peptide that is lethal to 100% of a cell culture). Such information can be used to more accurately determine useful doses in humans.

Initial dosages can also be estimated from in vivo data, e.g., animal models, using techniques that are well known in the art. One having ordinary skill in the art could readily optimize administration to humans based on animal data. In certain embodiments dosage amount and interval can be adjusted individually to provide plasma levels of the active peptide which are sufficient to maintain therapeutic effect.

In cases of local administration or selective uptake, the effective local concentration of peptide may not be related to plasma concentration. One having skill in the art will be able to optimize therapeutically effective local dosages without undue experimentation.

The antimicrobial therapy may be repeated intermittently while infections are detectable or even when they are not detectable. The therapy may be provided alone or in combination with other drugs, such as for example antibiotics or other antimicrobial peptides.

Toxicity

Preferably, a therapeutically effective dose of the AMPs and other constructs described herein will provide therapeutic benefit without causing substantial toxicity.

Toxicity can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds that exhibit high therapeutic indices are preferred, particularly for in vivo applications. The data obtained from cell culture assays and animal studies can be used in formulating a dosage range that is not toxic for use in human. The dosage of the peptides described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition (see, e.g., Fingl et al. (1975) In: The Pharmacological Basis of Therapeutics, Ch. 1, p. 1).

VII. Kits.

In another embodiment this invention provides kits for the inhibition of an infection and/or for the treatment and/or prevention of dental caries in a mammal and/or the inhibition of biofilms (e.g., on a prosthetic or medical implant). The kits typically comprise a container containing one or more of the active agents (i.e., antimicrobial peptides or compound antimicrobial peptides) described herein. In certain embodiments the active agent(s) can be provided in a unit dosage formulation (e.g., suppository, tablet, caplet, patch, etc.) and/or may be optionally combined with one or more pharmaceutically acceptable excipients.

In certain embodiments the kits comprise one or more of the home healthcare product formulations described herein (e.g., toothpaste, mouthwash, tooth whitening strips or solutions, contact lens storage, wetting, or cleaning solutions, dental floss, toothpicks, toothbrush bristles, oral sprays, oral lozenges, nasal sprays, aerosolizers for oral and/or nasal application, and the like).

In certain embodiments the kits comprise one or more of the disinfectant formulations described herein.

In addition, the kits optionally include labeling and/or instructional materials providing directions (i.e., protocols) for the practice of the methods or use of the "therapeutics" or "prophylactics" of this invention. Preferred instructional materials describe the use of one or more active agent(s) of this invention to therapeutically or prophylactically to inhibit or prevent infection and/or to inhibit the formation of dental caries. The instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Synthesis and Screening of Antimicrobial Peptides

Peptides were synthesized utilizing standard solid-phase synthesis methods (Fmoc or Boc chemistries). In certain embodiments, peptides were synthesized using Fmoc (9-fluorenylmethoxy carbonyl) solid-phase synthesis utilizing single or double coupling cycles at 0.01 to 0.25 mmol scales. Briefly, N-terminal deprotection was conducted in 20% (v/v) piperidine/N-methylpyrrolidone (NMP) for 3 min followed by eight washes with NMP. For the coupling cycle, amino acids were solubilized in 0.45 M N-hydroxybenzotrazole (HOBt)/HBTU (O-benzotriazole-N,N,N,N-tetramethyluronium hexafluoro-phosphate) in dimethylformamide (DMF) with 0.9 M diisopropyl ethylamine (DIEA) (1:1:1:2 ratio Fmoc amino acid:HOB:HBTU:DIEA) before being added to the resin for 30 min, followed by 10 NMP rinses. As needed, peptides were then labeled N-terminally with 4-molar excess fluorescent dyes or blocking groups in HOBt/HBTU/DIEA coupling solution with shaking at ambient temperature for 24 h followed by 10 rinses in dichloromethane (DCM).

After synthesis, the resin was washed 4× in DCM, 1× in MeOH, and dried 24 h under desiccant vacuum. Completed peptides were cleaved from the resin with 90% trifluoroacetic acid (TFA) and appropriate scavenging reagents. In some examples, D or L form amino acids, or a mixture of both, were used in synthesis. All peptides were purified by reverse-phase high-performance liquid chromatography (HPLC). Peptide mass was determined by electrospray ionization (ESI) mass spectrometry. Peptides were utilized in TFA salt form, acetate salt form, or HCl salt forms. Peptides were then screened for antimicrobial activity utilizing an MIC assay.

In certain embodiments the MIC assays are performed as follows: For each organism, the media and growth conditions utilized is detailed in Table 8. MIC tests were conducted in 96-well plates with 100 µL of bacterial or yeast suspension added in each well and challenged with twofold serial dilutions of peptide starting at 50 µM. After incubation 18-24 h, or in some cases 48 h, the lowest concentration at which the peptide inhibited bacterial and/or fungal growth was noted as the MIC (observation of a clear well by visual inspection).

In some cases killing kinetic experiments were then conducted. Killing kinetics of PF-S028 L and D versions against *M. furfur* were determined as described in Eckert et al. (2006) *Antimicrob Agents Chemother.*, 50: 1480-1488. Briefly, a log phase culture of *M. furfur* ATCC 14521 was diluted to $10^6$ cells/ml in ATCC medium 1072. To the reaction tubes 5 µM of either PF-S028 L or PF-S028 D were added. A reaction tube to which 4 µl of 50% methanol was added served as the negative control. Reaction tubes were stored at 30° C. and at indicated intervals a sample was removed from the reaction tube and placed in a recovery tube where peptide was removed by dilution. An aliquot from the recovery tube was plated on ATCC medium 1072 agar plates and incubated at 30° C. until visible colonies formed. Colony forming units were calculated for the negative control (no peptide), PF-S028 L, and PF-S028 D treated cultures. After 15 min of treatment, PF-S028 D killed over 99% of the *M. furfur*. PF-S028 L killed 39% (FIG. 1).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated antimicrobial peptide having antimicrobial activity against at least one kind of bacteria, fungus, or yeast, said antimicrobial peptide ranging in length up to 25 amino acids wherein the amino acid sequence of said peptide comprises the sequence SLQSQLGPCLHDQRH (PF-448, SEQ ID NO:19), and wherein said peptide has antimicrobial activity against *Streptococcus pneumoniae*.

2. The antimicrobial peptide of claim 1, wherein the amino acid sequence of said peptide consists of the amino acid sequence SLQSQLGPCLHDQRH (PF-448, SEQ ID NO:19).

3. The antimicrobial peptide of claim 1, wherein said peptide comprises all "L" amino acids.

4. The antimicrobial peptide of claim 1, wherein said peptide comprises all "D" amino acids.

5. The antimicrobial peptide of claim 1, wherein said peptide is a β peptide.

6. The antimicrobial peptide of claim 1, wherein said peptide comprises one or more protecting groups.

7. The antimicrobial peptide of claim 1, wherein said peptide is in a pharmaceutically acceptable carrier.

8. The antimicrobial peptide according to claim 7, wherein said carrier is suitable for administration via a route selected from the group consisting of topical administration, aerosol administration, administration via inhalation, oral administration, systemic IV application, ocular administration, and rectal administration.

9. A method of killing and/or inhibiting the growth and/or proliferation of a microorganism, said method comprising contacting said microorganism with a peptide of claim 1.

* * * * *